US010941403B2

(12) United States Patent
Anand et al.

(10) Patent No.: US 10,941,403 B2
(45) Date of Patent: Mar. 9, 2021

(54) MICRORNA INHIBITORS AS ANTI-CANCER THERAPEUTICS

(71) Applicant: Oregon Health & Science University, Portland, OR (US)

(72) Inventors: Sudarshan Anand, Portland, OR (US); Shushan Rana, Portland, OR (US); Charles R. Thomas, Jr., Portland, OR (US)

(73) Assignee: Oregon Health & Science University, Portland, OR (US)

( * ) Notice: Subject to any disclaimer, the term of this patent is extended or adjusted under 35 U.S.C. 154(b) by 0 days.

(21) Appl. No.: 16/373,452

(22) Filed: Apr. 2, 2019

(65) Prior Publication Data
US 2019/0300883 A1    Oct. 3, 2019

Related U.S. Application Data

(60) Provisional application No. 62/651,669, filed on Apr. 2, 2018.

(51) Int. Cl.
*C12N 15/113* (2010.01)
*A61P 35/00* (2006.01)

(52) U.S. Cl.
CPC .......... *C12N 15/1135* (2013.01); *A61P 35/00* (2018.01); *C12N 2310/113* (2013.01)

(58) Field of Classification Search
None
See application file for complete search history.

(56) References Cited

U.S. PATENT DOCUMENTS

| 8,367,381 | B2 | 2/2013 | Smith et al. | |
| 9,163,235 | B2 | 10/2015 | Rooij et al. | |
| 2008/0233567 | A1* | 9/2008 | Murray | G01N 33/574 435/6.14 |
| 2009/0131356 | A1* | 5/2009 | Bader | C12N 15/111 514/44 R |
| 2010/0029003 | A1 | 2/2010 | Bartel et al. | |
| 2012/0190730 | A1 | 7/2012 | Michael | |
| 2012/0283310 | A1 | 11/2012 | Croce et al. | |
| 2015/0322529 | A1 | 11/2015 | Ghobrial et al. | |
| 2019/0062754 | A1 | 2/2019 | Ju et al. | |

FOREIGN PATENT DOCUMENTS

WO    2017152182 A1    9/2017

OTHER PUBLICATIONS

Bonci et al., The miR-15a-miR-16-1 cluster controls prostate cancer by targeting multiple oncogenic activities, Nature Medicine, vol. 14, No. 11, Nov. 2008, pp. 1271-1277.
Chaudry et al., Radiation-Induced Micro-RNA Modulation in Glioblastoma Cells Differing in DNA-Repair Pathways, DNA and Cell Biology, vol. 29, No. 9, 2010, pp. 553-561.
Hafner et al., Transcriptome-wide Identification of RNA-Binding Protein and MicroRNA Target Sites by PAR-CLIP, Cell, 141, Apr. 2, 2010, pp. 129-141.
Jin et al., miR-15a-5p acts as an oncogene in renal cell carcinoma, Molecular Medicine Reports, 15, 2017, pp. 1379-1386.
Kontos et al., miR-15a-5p, A Novel Prognostic Biomarker, Predicting Recurrent Colorectal Adenocarcinoma, Mol Diagn Ther (2017) 21:453-464.
Lan et al., miR-15a/16 Enhances Radiation Sensitivity of Non-Small Cell Lung Cancer Cells by Targeting the TLR1/NF-kB Signaling Pathway, Int J Radiation Oncol Biol Phys, vol. 91, No. 1, pp. 73e81, 2015.
Liu et al., MiR-15a contributes abnormal immune response in myasthenia gravis by targeting CXCL10, Clinical Immunology 164 (2016) 106-113.
Mei et al., The miR-15 Family Enhances the Radiosensitivity of Breast Cancer Cells by Targeting G2 Checkpoints, Radiation Research 183, 196-207 (2015).
Moon et al., miR-15a/16 Regulates Macrophage Phagocytosis after Bacterial Infection, Journal of Immunology, Journal of Immunology, Nov. 2014, 193(9), pp. 4558-4567.
Pengcheng et al., MicroRNA-497 suppresses renal cell carcinoma by targeting VEGFR-2 in ACHN cells, Bioscience Reports (2017) 37, pp. 1-10.
Rocarro et al., MicroRNAs 15a and 16 regulate tumor proliferation in multiple myeloma, BLOOD, Jun. 25, 2009 vol. 113, No. 26, pp. 6669-6680.
Rouholamini et al., Inhibition of mir-15a Gene Expression by Silibinin in MCF-7 Breast Cancer Cell Line, Int.J.Curr.Res.Aca. Rev.2015; 3(10): pp. 288-296.
Sambri et al., The MicroRNA 15a/16-1 Cluster Down-regulates Protein Repair Isoaspartyl Methyltransferase in Hepatoma Cells, The Journal of Biological Chemistry vol. 286, No. 51, pp. 43690-43700, Dec. 23, 2011.
Svoronos et al., OncomiR or Tumor Suppressor? The Duplicity of MicroRNAs in Cancer, Cancer Res; 76(13) Jul. 1, 2016, pp. 3666-3670.
Tian et al., MiRNA-15a inhibits proliferation, migration and invasion by targeting TNFAIP1 in human osteosarcoma cells, Int J Clin Exp Pathol 2015;8(6):6442-6449.
Xiao et al., Aberrant Expression of MicroRNA-15a and MicroRNA-16 Synergistically Associates with Tumor Progression and Prognosis in Patients with Colorectal Cancer, Gastroenterology Research and Practice, vol. 2014, Article ID 364549, Published online Nov. 4, 2014, 8 pages, doi: 10.1155/2014/364549, PMCID: PMC4236961.
Xie et al., MicroRNA-15a down-regulation is associated with adverse prognosis in human glioma, Clin Transl Oncol (2015)17:504-510.
Yang et al., MiR-15a/16 deficiency enhances anti-tumor immunity of glioma-infiltrating CD81 T cells through targeting mTOR, Int. J. Cancer: 141, 2082-2092 (2017).

(Continued)

*Primary Examiner* — Brian Whiteman

(57) ABSTRACT

MicroRNA inhibitors as anti-cancer therapeutics are described. The microRNA inhibitors can inhibit microRNA-15a and can mimic the effects of higher dose radiation at lower doses. Other benefits are also described.

15 Claims, 24 Drawing Sheets

Specification includes a Sequence Listing.

(56) References Cited

OTHER PUBLICATIONS

Zhang et al., Influence of Recombinant Lentiviral Vector Encoding miR-15a/16-1 in Biological Features of Human Nasopharyngeal Carcino . . . , Cancer Biotherapy and Radiopharmaceuticals, vol. 29, No. 10, 2014, pp. 422-427.

Zhu et al., MicroRNA-15a Inhibits Proliferation and Induces Apoptosis in CNE1 Nasopharyngeal Carcinoma Cells, Oncology Research, 24(3), 2016, pp. 145-151.

* cited by examiner

| ~2 fold increase | ~100 fold decrease |
|---|---|
| ↓ SMPD1 | ↑ SMPD1 |
| ↓ ceramide | ↑ceramide |
| ↓ ASMase | ↑ ASMase |
| ↓ apoptosis | ↑apoptosis |

SEQUENCE LISTING

```
<160> NUMBER OF SEQ ID NOS: 1

<210> SEQ ID NO 1
<211> LENGTH: 22
<212> TYPE: RNA
<213> ORGANISM: Artificial Sequence
<220> FEATURE:
<223> OTHER INFORMATION: Synthetic Oligonucleotide: complementary to
      human miR-15a

<400> SEQUENCE: 1
cacaaaccau uaugugcugc ua                                              22
```

MICRORNA INHIBITORS AS ANTI-CANCER THERAPEUTICS

CROSS-REFERENCE TO RELATED APPLICATIONS

This application claims priority to U.S. Provisional Patent Application No. 62/651,669, filed Apr. 2, 2018.

FIELD OF THE DISCLOSURE

MicroRNA inhibitors as anti-cancer therapeutics are described. The microRNA inhibitors can inhibit microRNA-15a and can mimic the effects of higher dose radiation at lower doses. Other benefits are also described.

BACKGROUND OF THE DISCLOSURE

Almost 50% or all cancer patients undergo some form of radiotherapy. However only half of these patients have significant responses to radiation. While several specific options exist to escalate the dose of radiation (e.g., stereotactic body radiation therapy, SBRT or stereotactic radiosurgery, SRS) while minimizing damage to normal organs, including the heart, often this is not feasible due to the location of tumor, organ site etc.). Therefore approaches to enhance the efficacy of lower (conventional dose radiation) are valuable.

SUMMARY OF THE DISCLOSURE

The current disclosure provides that microRNA-15a inhibition can be used as an anti-cancer therapeutic. In particular embodiments microRNA-15a inhibition enhances the efficacy of lower (conventional dose) radiation. The current disclosure shows that miR-15a inhibition decreases cell proliferation and increases cell death in endothelial cells and cancer cells. Treatment of tumor bearing mice with an miR-15a inhibitor decreased tumor growth. In particular embodiments, miR15a inhibition can mimic the effects of higher dose radiation and increase tumor and endothelial cell killing.

BRIEF DESCRIPTION OF THE SEVERAL VIEWS OF THE DRAWINGS

Certain of the drawings submitted herein are better understood in color, which is not available in patent application publications at the time of filing. Applicants consider the color versions of the drawings as part of the original submission and reserve the right to present color images of the drawings in later proceedings.

Figure 2:
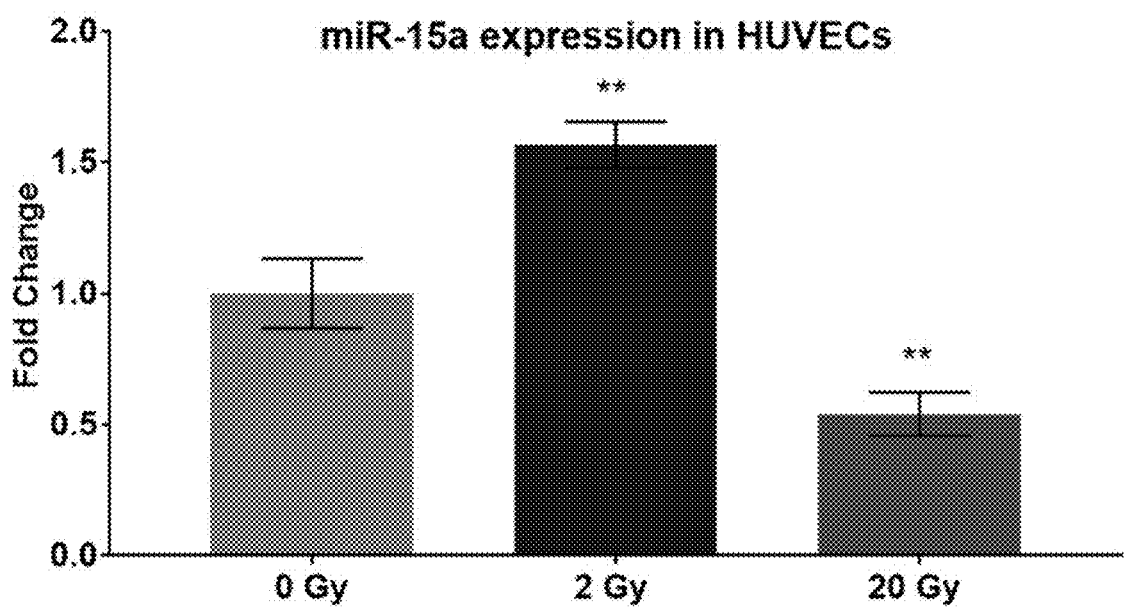
FIG. 2. miR-15a and SMPD1 expression in HUVECS. A. miR-15a expression 6 h post radiation to HUVECS. Fold change relative to 0 Gy expression. p<0.01 per post-ANOVA Dunnett's multiple comparison test. B. SMPD1 mRNA is downregulated by miR-15a in HUVECs. Transfection of miR-15a mimic was compared to its respective scrambled miRNA control *p<0.001 per ANOVA.
Figure 2:
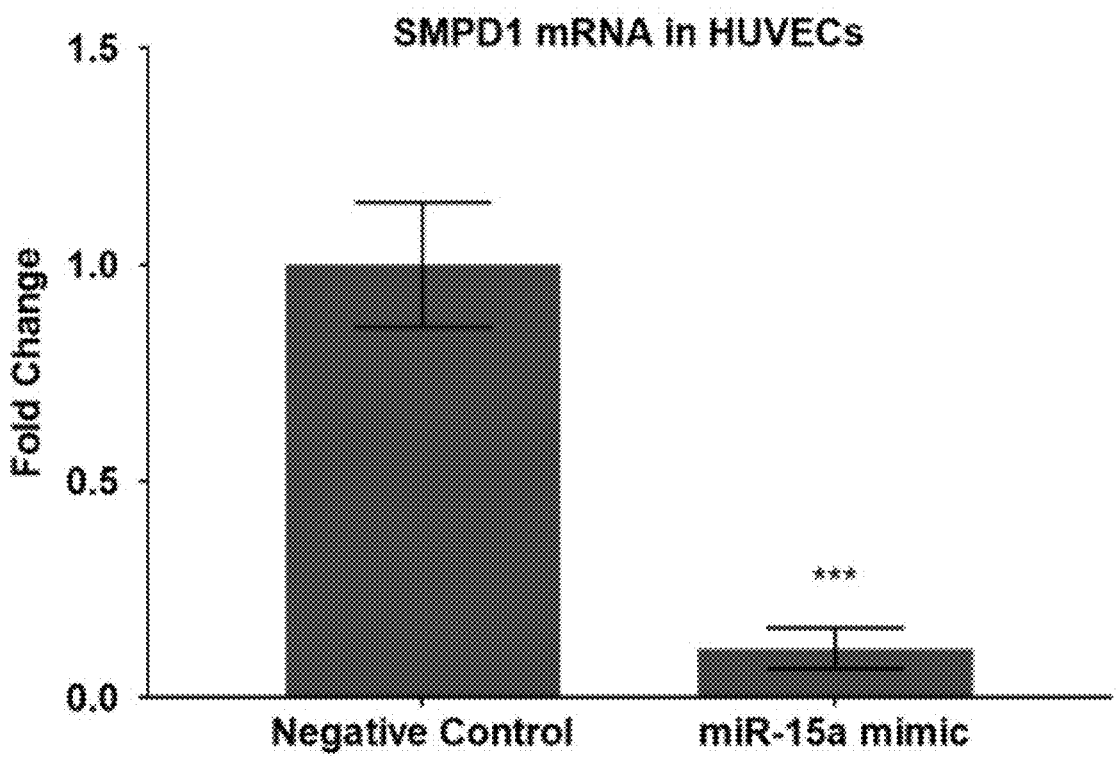
Figure 3:
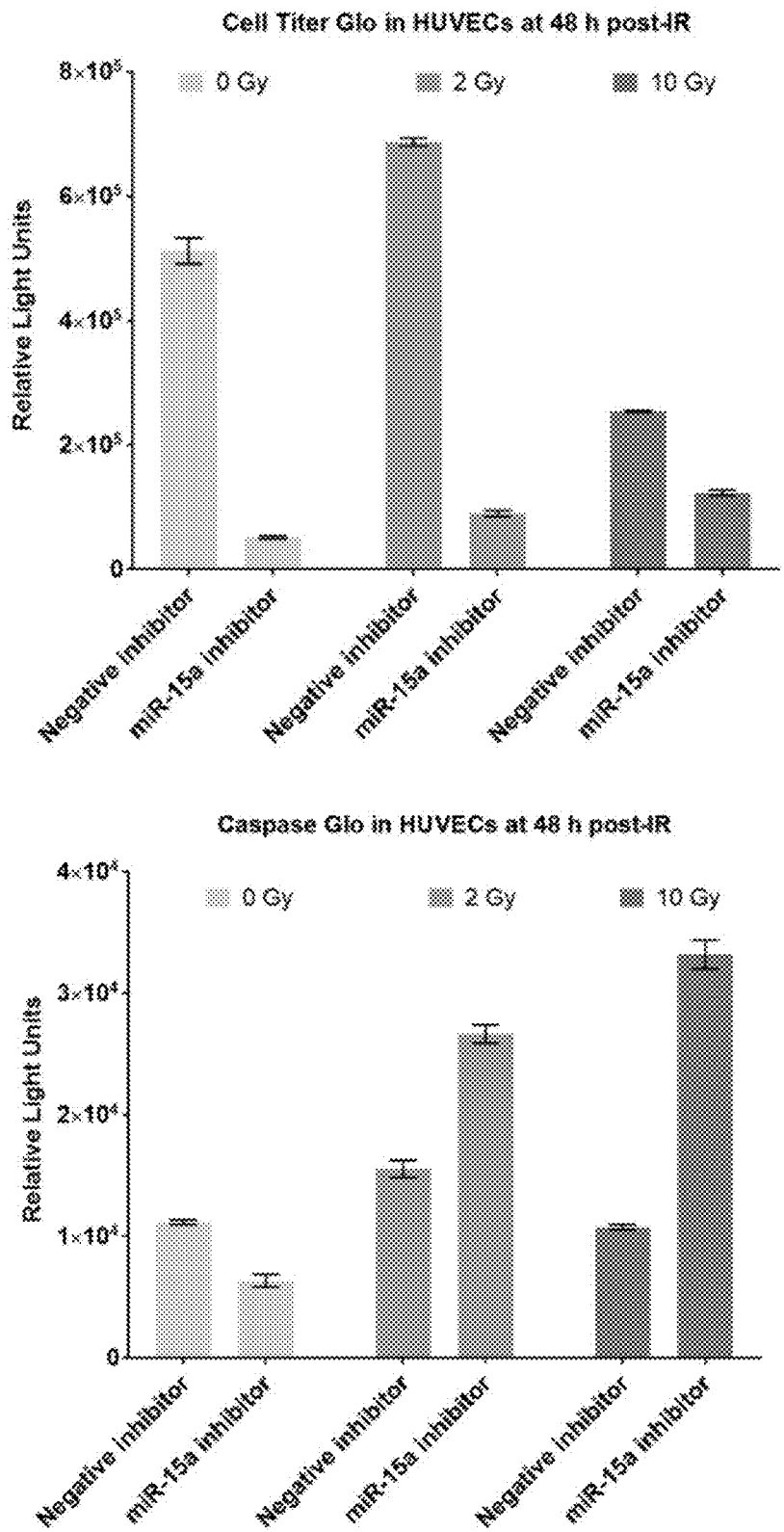
FIG. 3. Inhibition of miR-15a decreases EC proliferation and viability. A. HUVECs were transfected with either a control negative inhibitor or a miR-15a inhibitor. 24 h after transfection, cells were irradiated with either a 2 Gy or 10 Gy dose in a single fraction. 48 h post radiation proliferation (upper panel) or cell death (lower panel) was measured using a luciferase based cell titer glo (A) assay or Caspase 3 & 7 CasGlo assay. Bars indicate means±SEM of 3 technical replicate wells. One of at least two independent experiments is shown.
Figure 4:
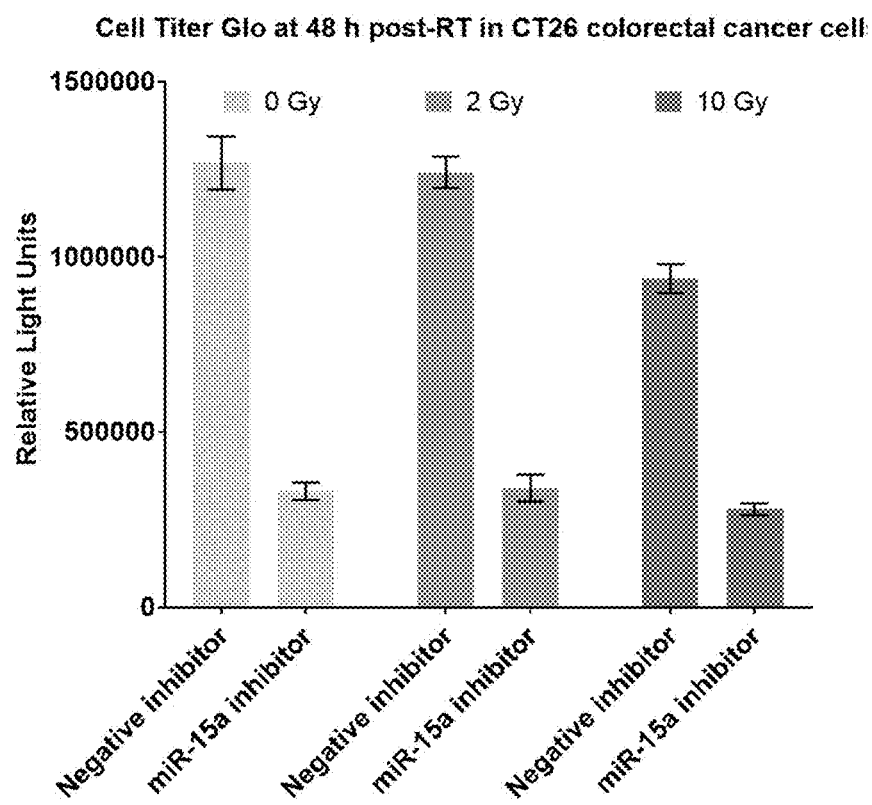
FIG. 4. Top panel. Inhibition of miR-15a decreases tumor cell proliferation and tumor burden in vivo. Inhibition of miR-15a decreased cellular viability of CT26 colorectal cancer cells. Bars indicate means±SEM of 3 technical replicate wells. One of at least two independent experiments is shown. Bottom panel. CT26 tumors were implanted subcutaneously in Balb/C mice (N=5 mice per group, two tumors per mouse). Once tumors reached 100 mm$^3$ volume, mice were randomly assigned to either a negative control inhibitor group or a miR-15a inhibitor (20 mg/kg, i.v. in PBS). Mice were treated every two days for a total of three treatments. ***p<0.01; ANOVA on the day 7 tumor volumes.
Figure 4:
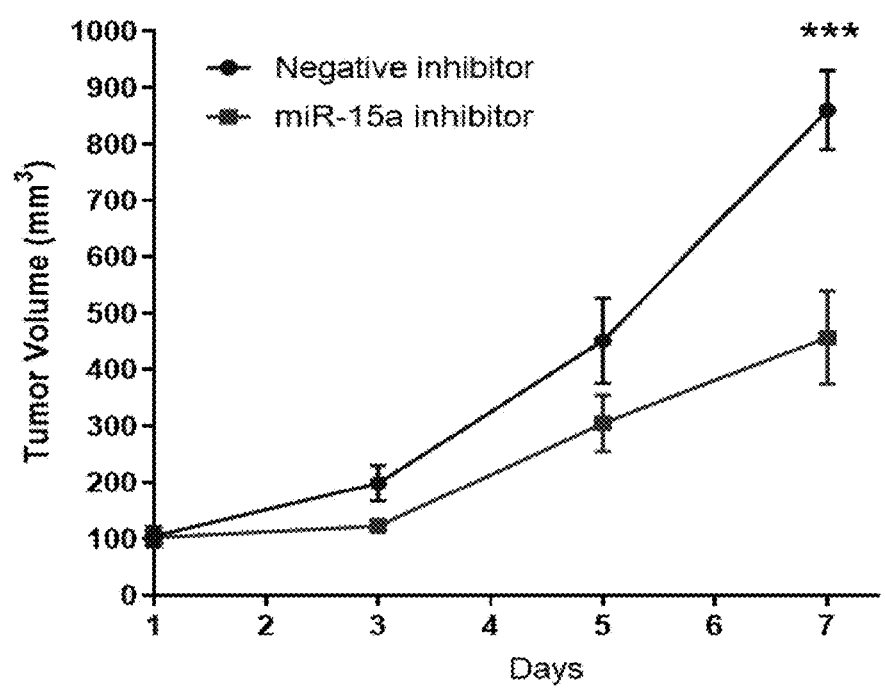

The data presented in FIGS. 5-8 may partially overlap with that presented in previous FIGS. 2-4.

Figure 5:
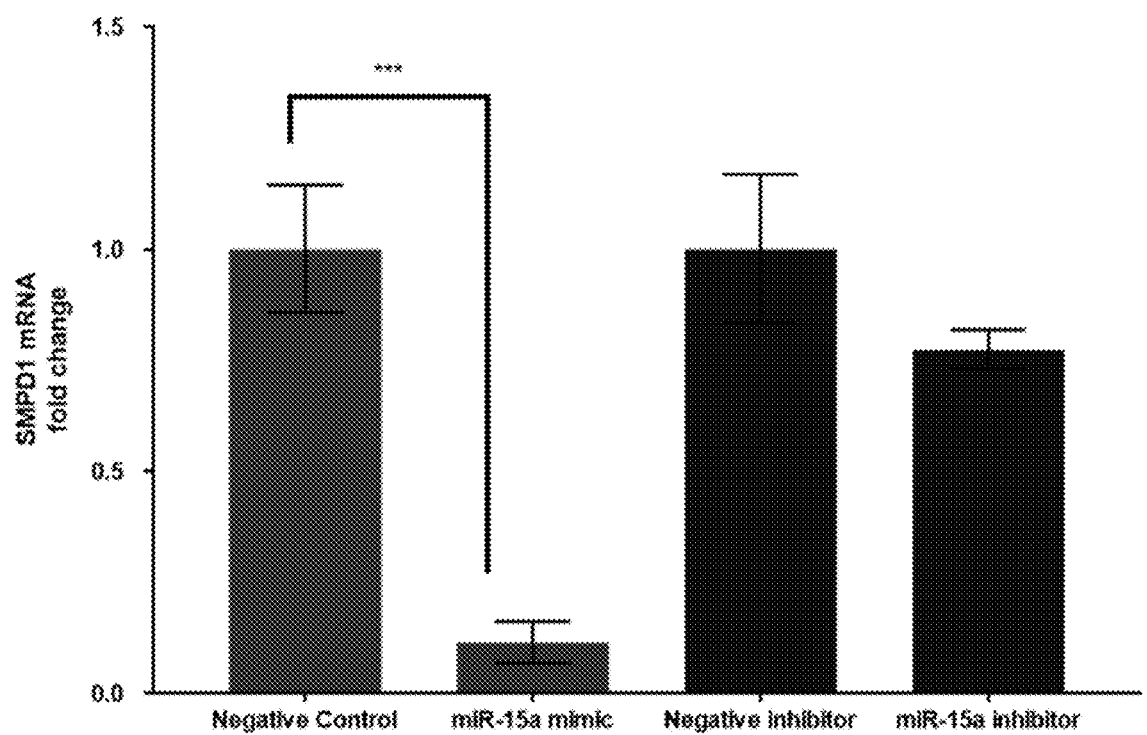

FIG. 5. SMPD1 mRNA is downregulated by miR-15a in HUVECs. Transfection of miR-15a and inhibitor of miR-15a were compared to their respective scrambled miRNA controls ***p<0.001 per ANOVA.

Figure 6:
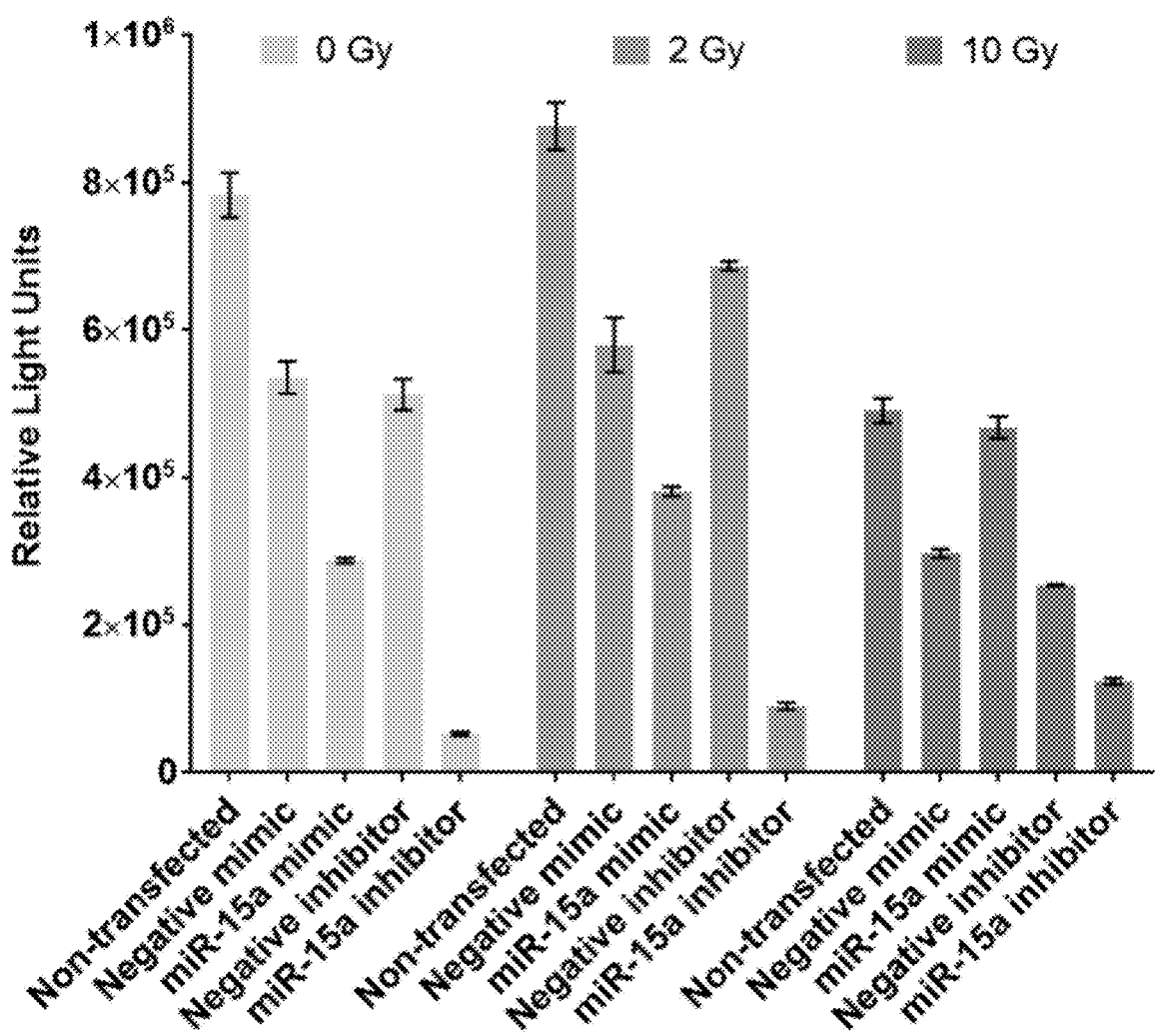

FIG. 6. Inhibition of miR-15a decreased cellular viability of HUVECs. Cells were transfected per the aforementioned miRNAs and underwent either no irradiation, 2 Gy, or 10 Gy irradiation 24 h post transfection. Relative light units were measured at 48 h post-IR and correlate to enzymatic fluorescent activity under the Cell Titer Glo assay and corresponds to phosphorylation activity as a surrogate for cellular activity.

Figure 7:
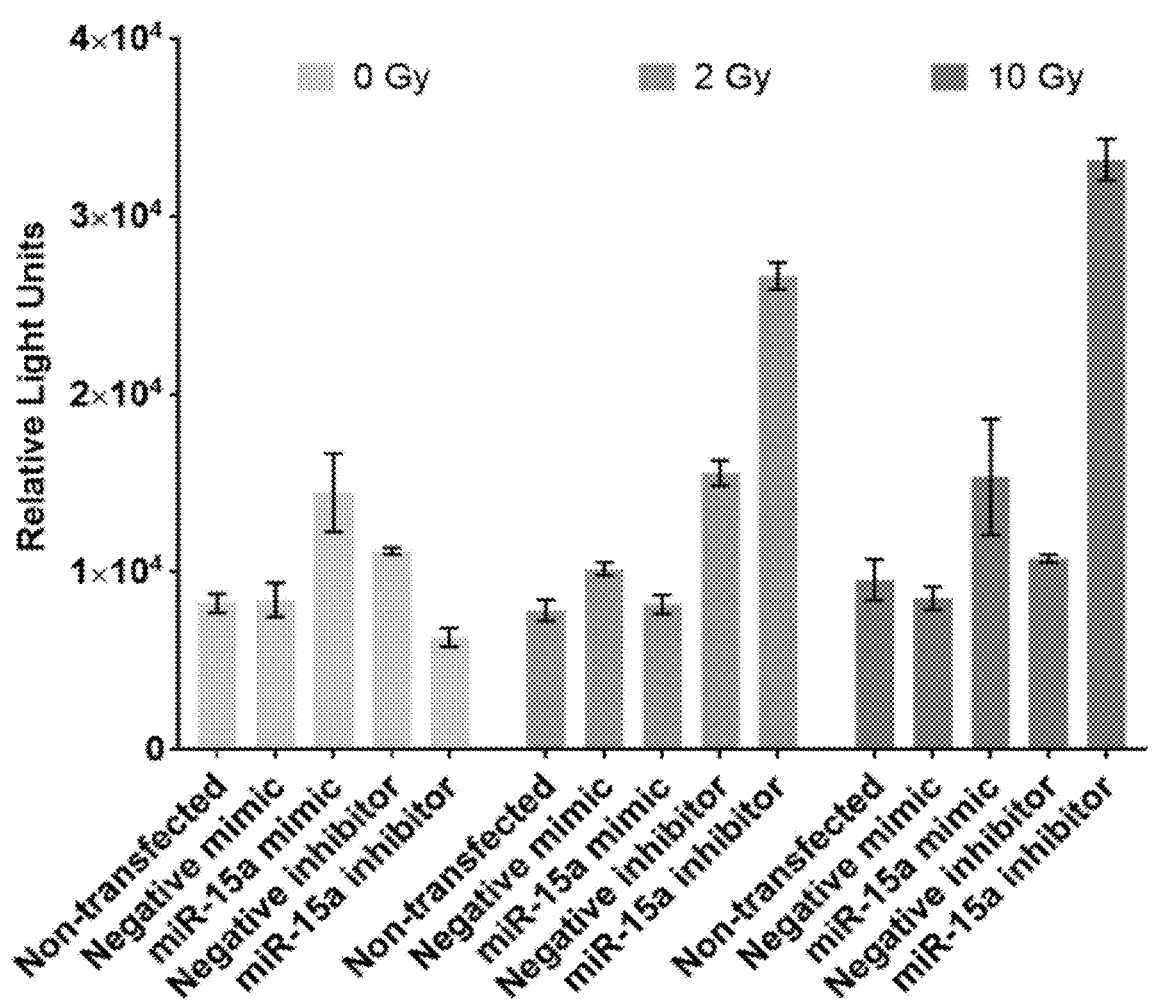

FIG. 7. Inhibition of miR-15a and radiation increases apoptosis in HUVECs. Cells were transfected per the aforementioned miRNAs and underwent either no irradiation, 2 Gy, or 10 Gy irradiation 24 h post transfection. Relative light units were measured at 48 h post-IR and correlate to enzymatic fluorescent activity under the Caspase Glo assay and corresponds to caspase 3 and 7 activity.

Figure 8:
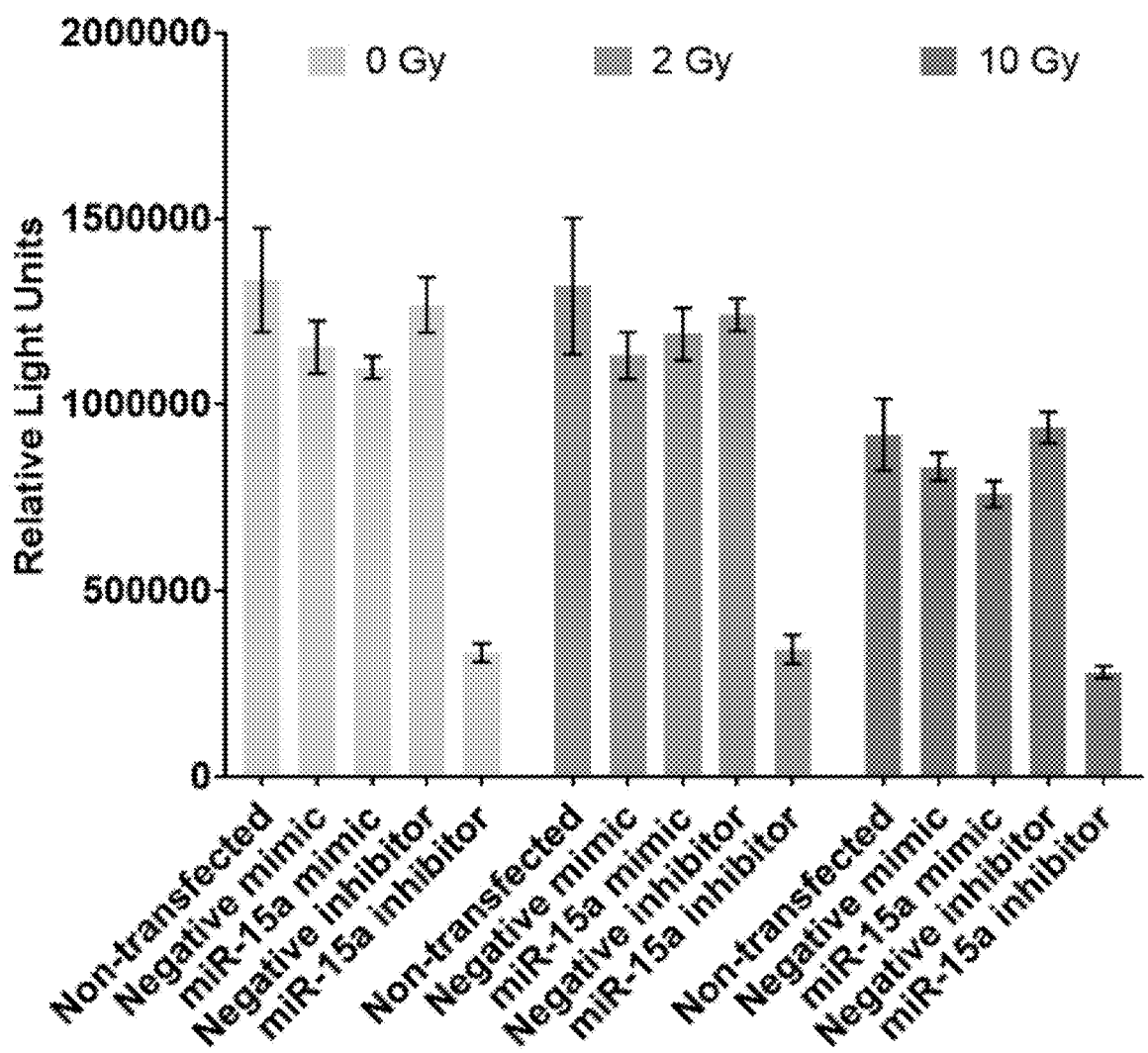

FIG. 8. Inhibition of miR-15a decreased cellular viability of CT26 colorectal cancer cells.

Figure 9A:
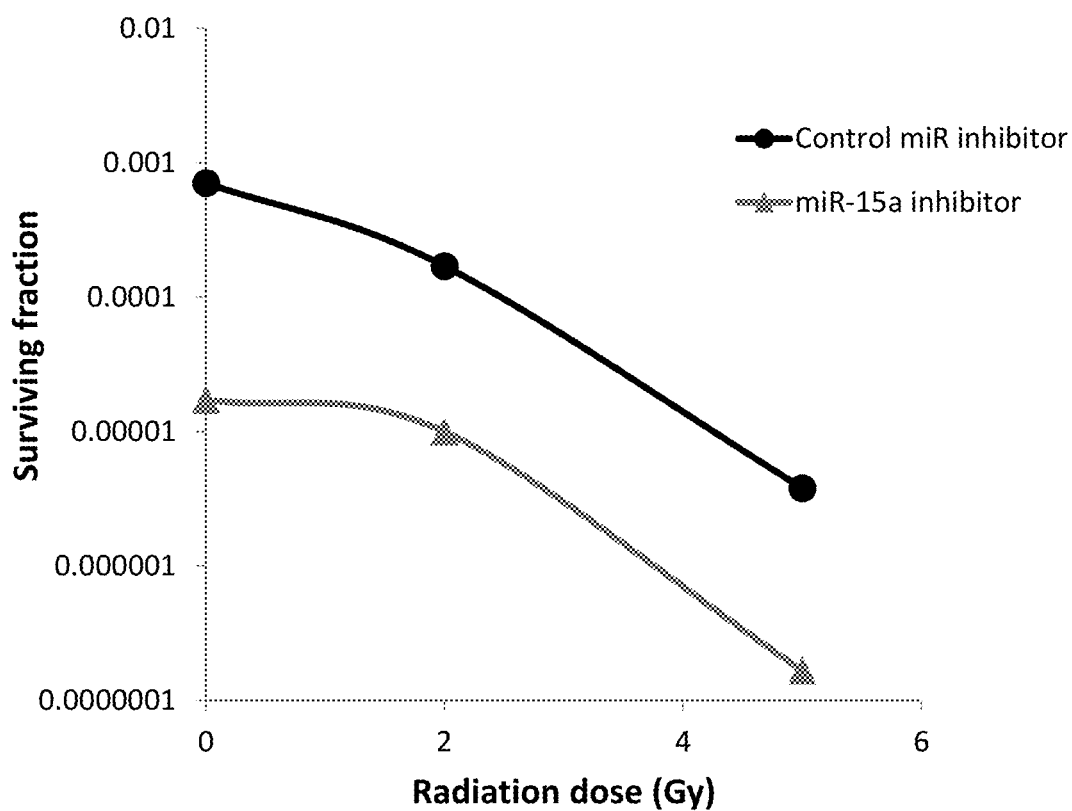
Figure 9B:
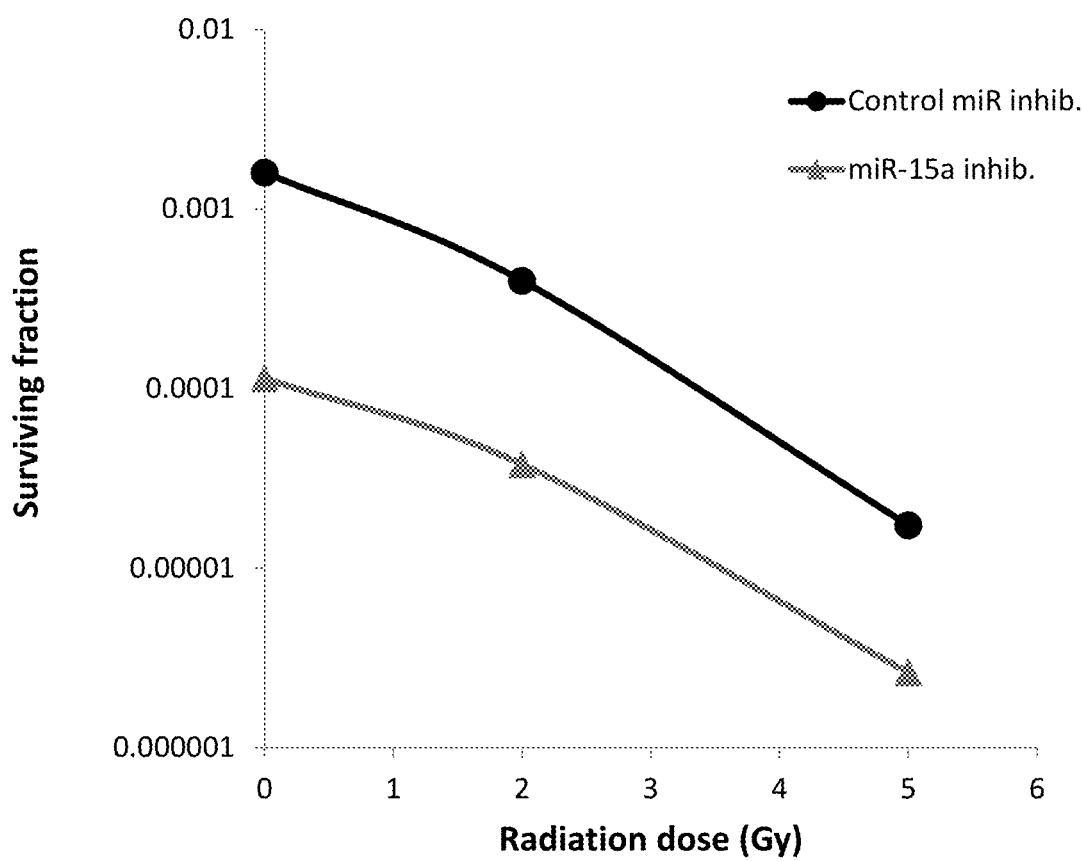

FIG. 9A, 9B. HCT116 were transfected with a miR-15a inhibitor or a control miR inhibitor from different vendors as indicated and plated on a 6-well plate. 12-14 days after plating, cells were fixed and stained with crystal violet and colonies were counted. Surviving fraction was calculated based on the colony numbers normalized to the plating efficiency. Mean of triplicate wells is plotted. (FIG. 9A) Effect of Exiqon SEQ ID NO: 1 inhibitor. (FIG. 9B) Effect of IDT SEQ ID NO: 1 inhibitor.

Figure 10A:
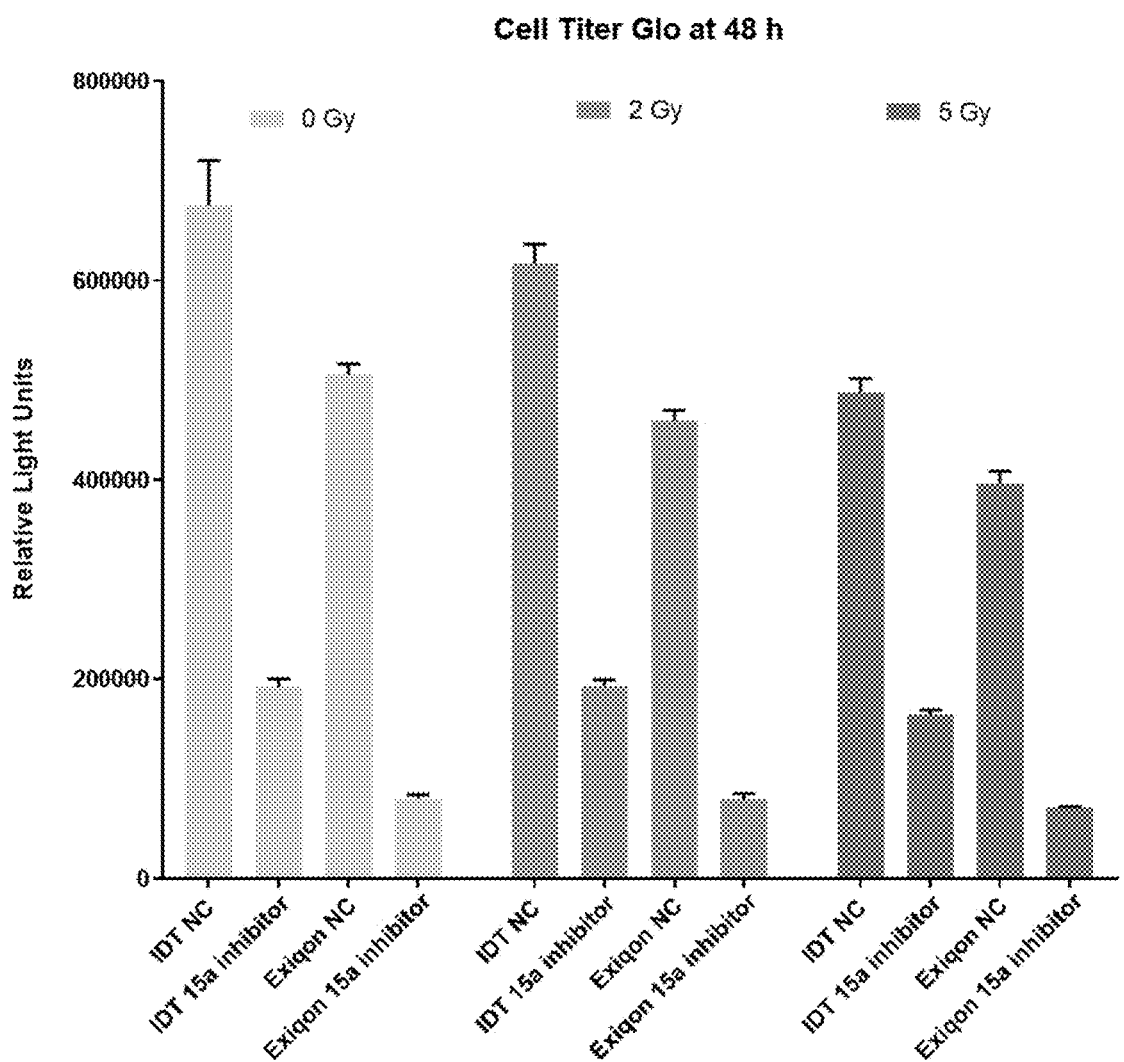
Figure 10B:
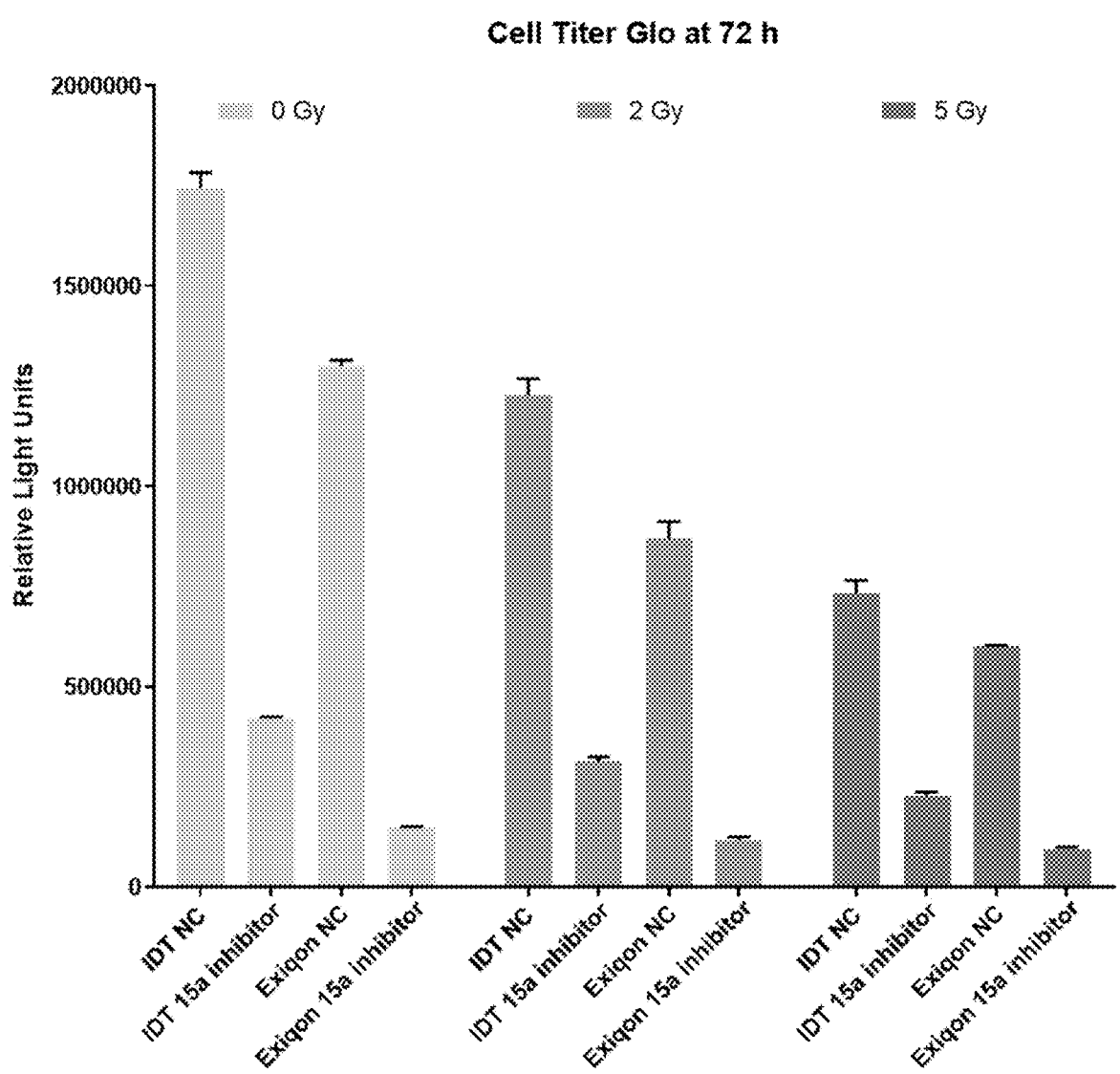

FIG. 10A, 10B. miR-15a inhibition decreases cell viability in HCT-116: a human colorectal cancer cell line at 48 (FIG. 10A) and 72 h (FIG. 10B).

Figure 11:
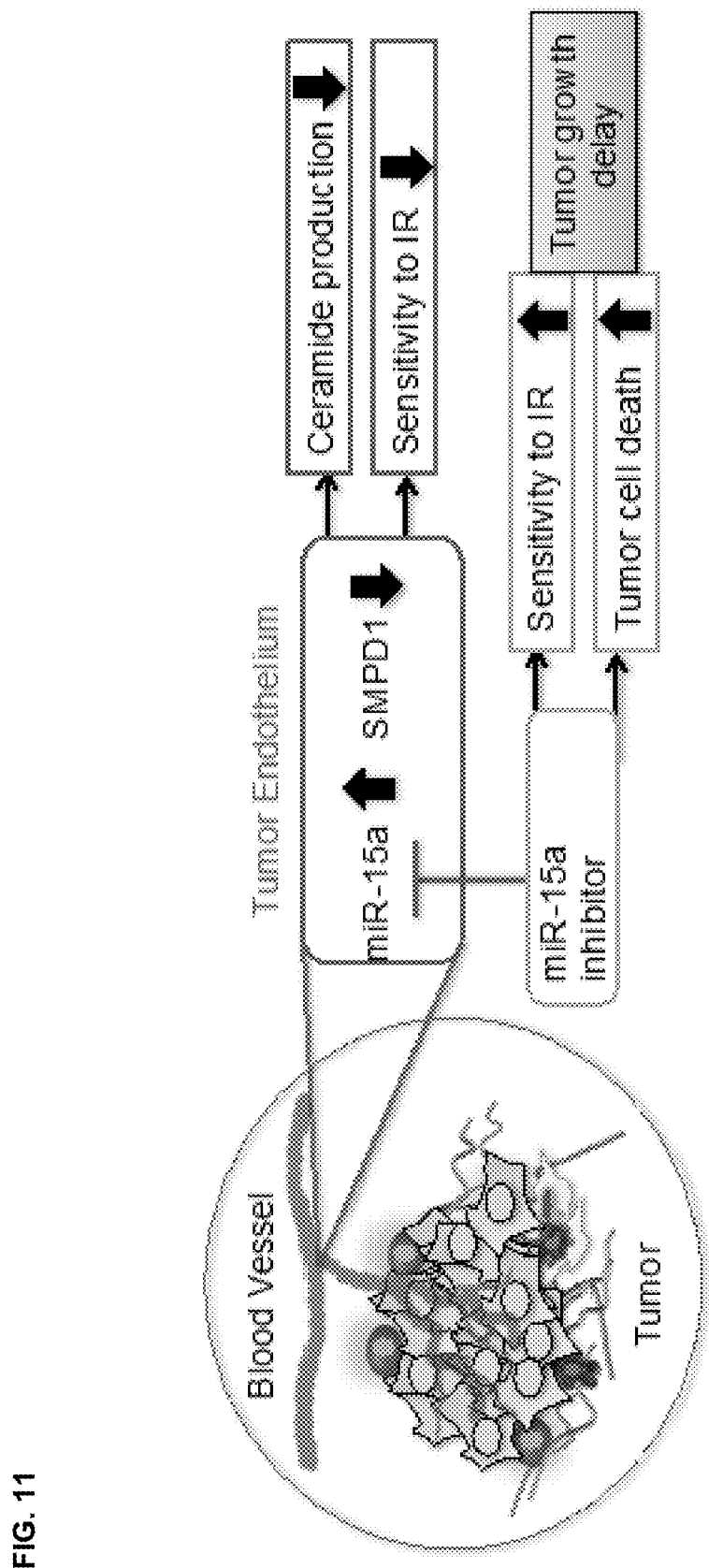

FIG. 11 illustrates proposed effects of miR-15a inhibition in tumor microenvironment.

Figure 12:
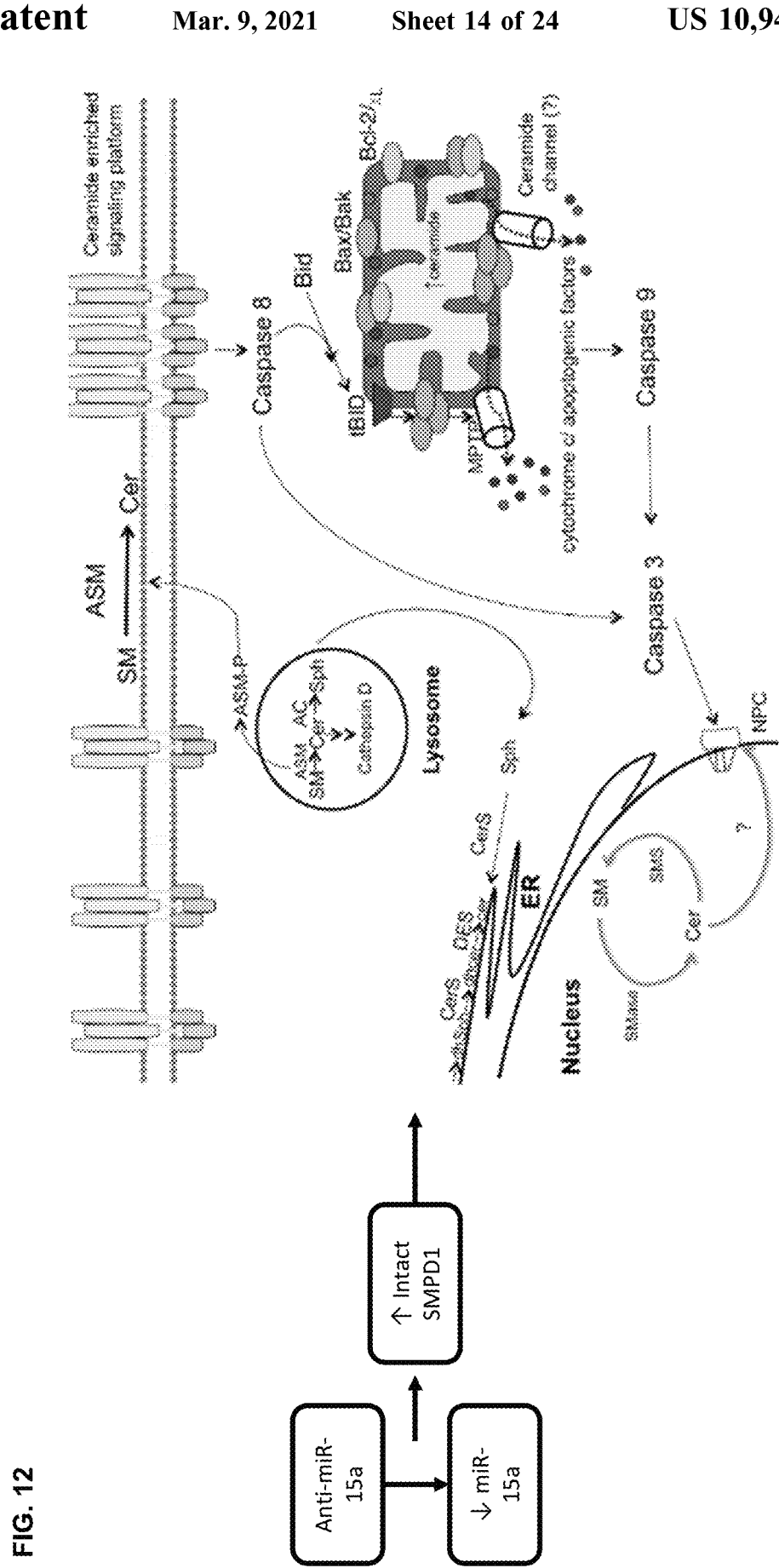

FIG. 12 depicts non-limiting mechanisms of action. Anti-miR-15a will increase endothelial cell apoptosis through prevention of miR-15a inhibition of SMPD1.

Figure 13A:
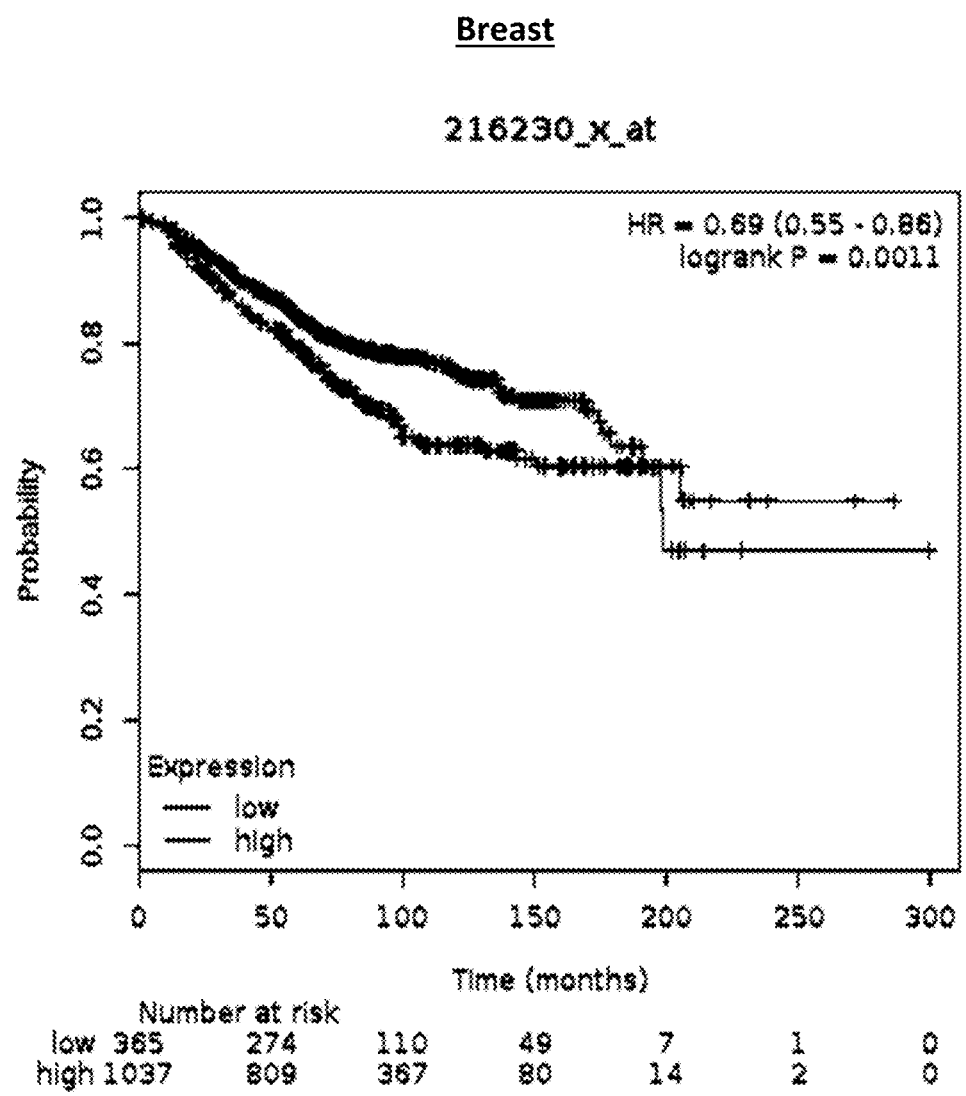
Figure 13B:
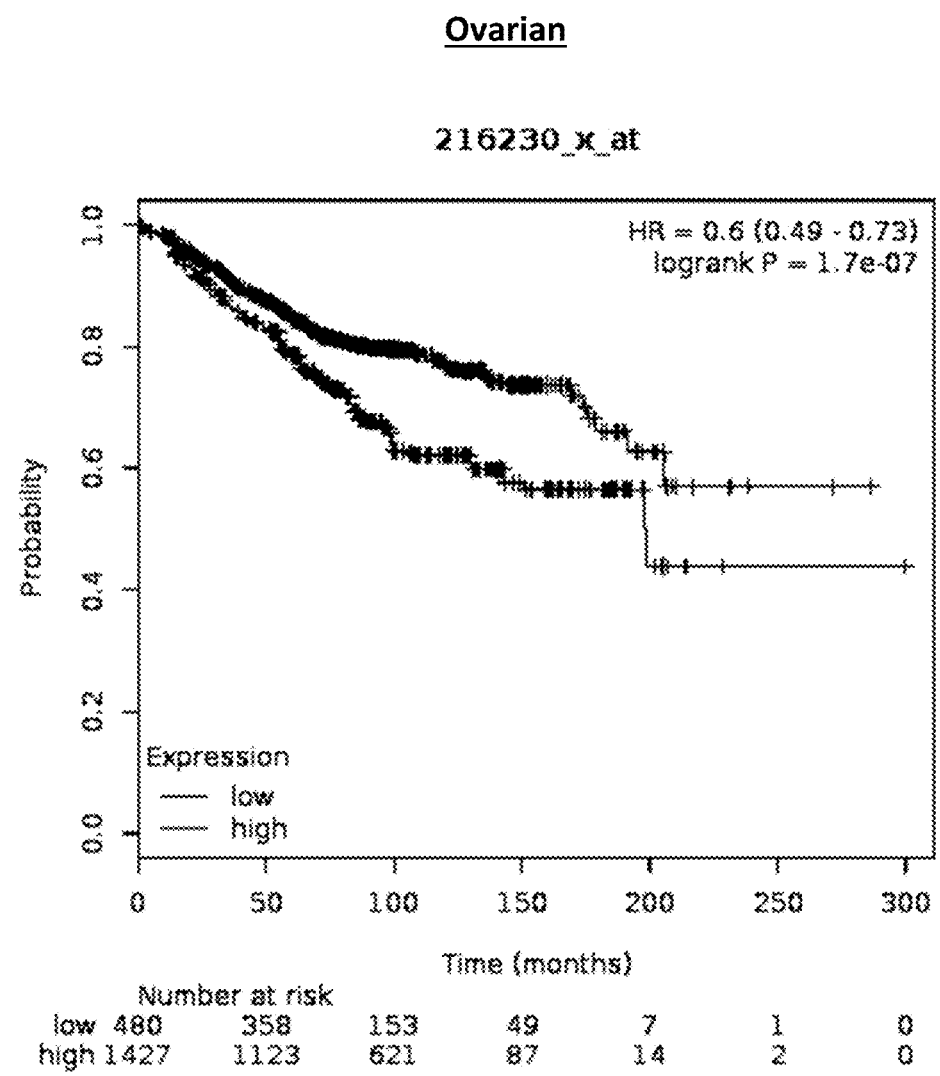
Figure 13C:
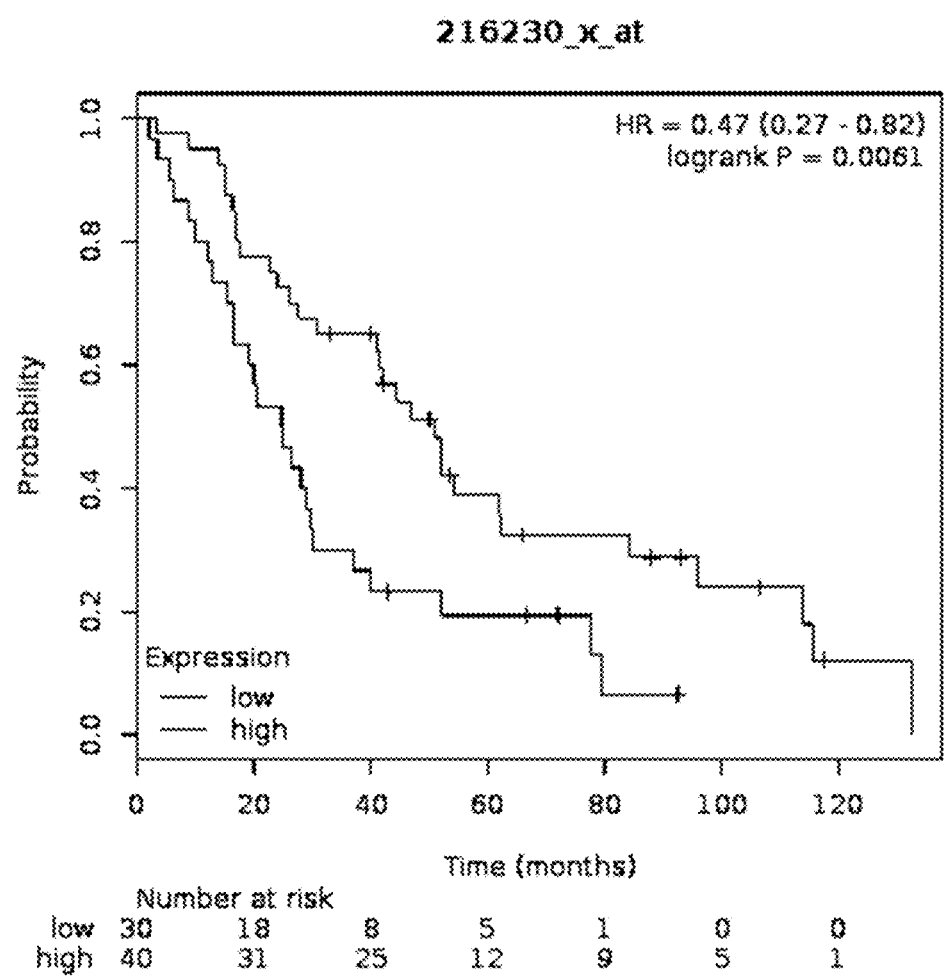

FIGS. 13A, 13B, and 13C depict levels of SMPD1 correlated with overall survival.

Figures 14A, 14B:

FIG. 14A depicts TargetScan analysis of the SMPD1 3' untranslated region identifying miR-15 family as putative regulators of SMPD1.

FIG. 14B demonstrates miR-15a exhibiting the greatest differential change at 6 hours post-IR between exposure of 2 Gy and 20 Gy radiation relative to non-irradiated samples.

Figure 15A:
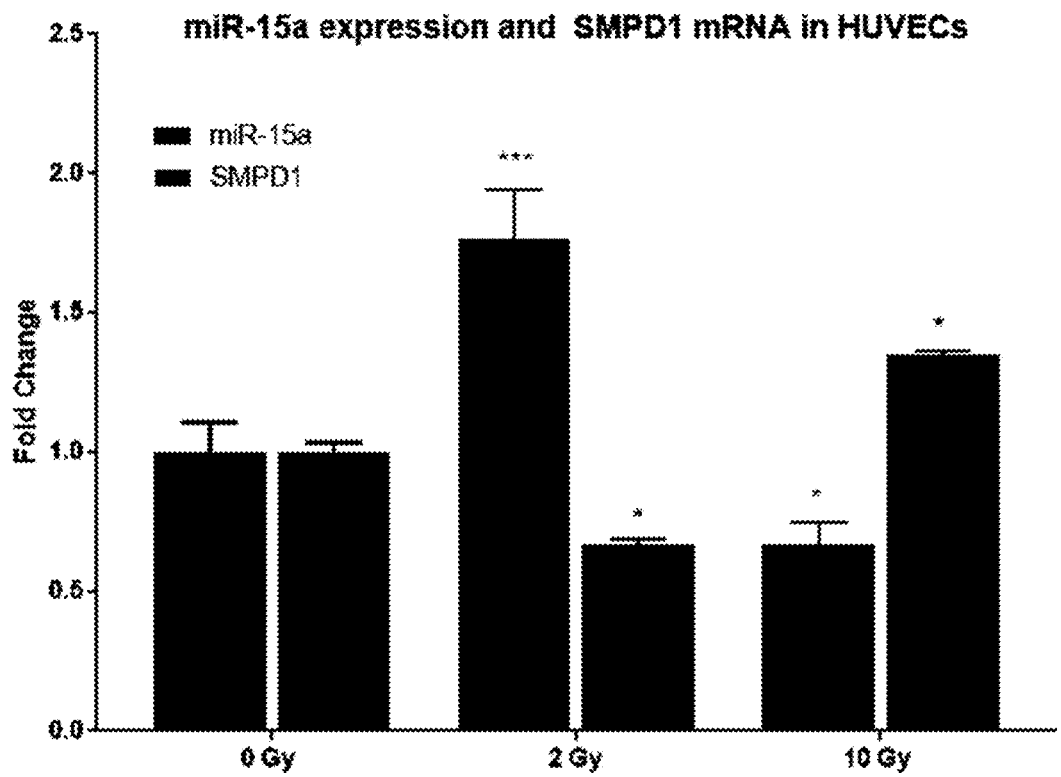
Figure 15B:
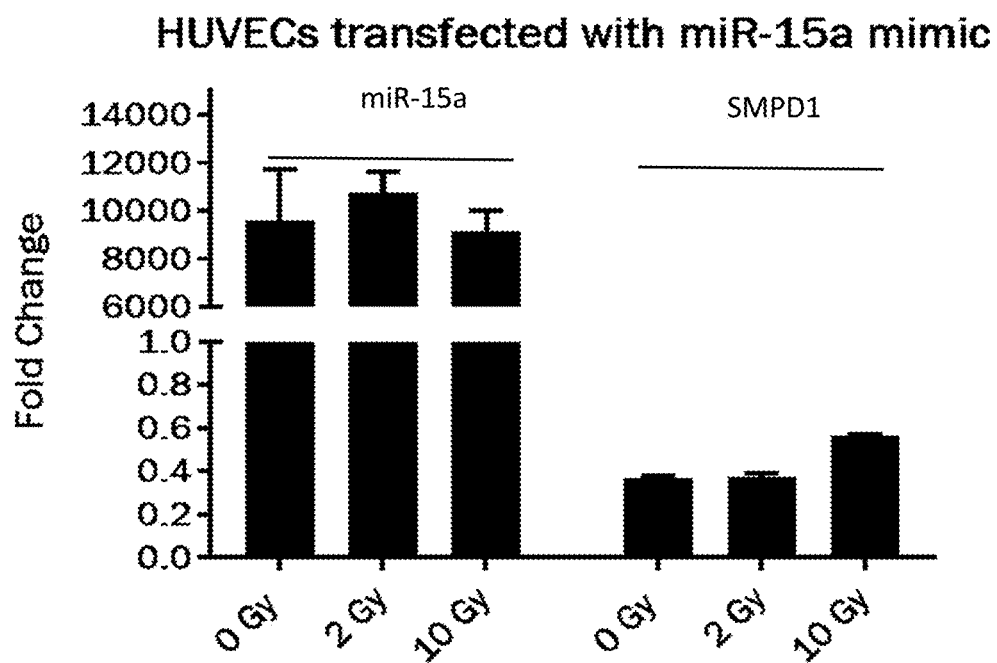
Figure 15C:
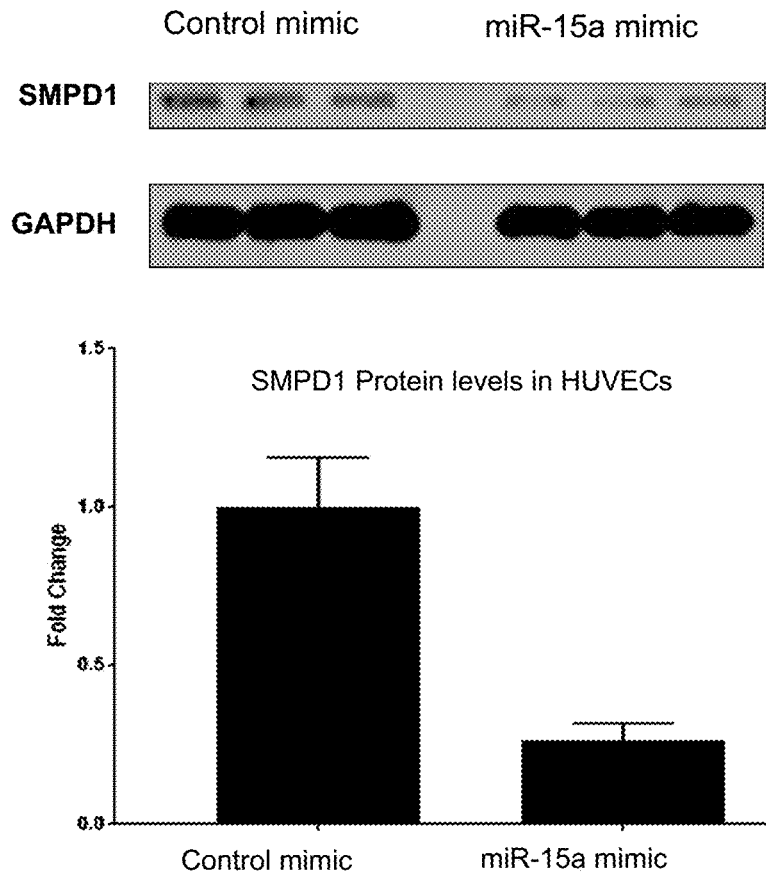

FIGS. 15A, 15B, and 15C illustrate endogenous miR-15a decreasing at high dose radiation and the expression of SMPD1 was reciprocal to the amount of miR-15a (FIG. 15A) via qRT-PCR and exogenous transfection of miR-15a reduced expression of SMPD1 mRNA (FIG. 15B) and protein levels (FIG. 15C).

Figure 16A:
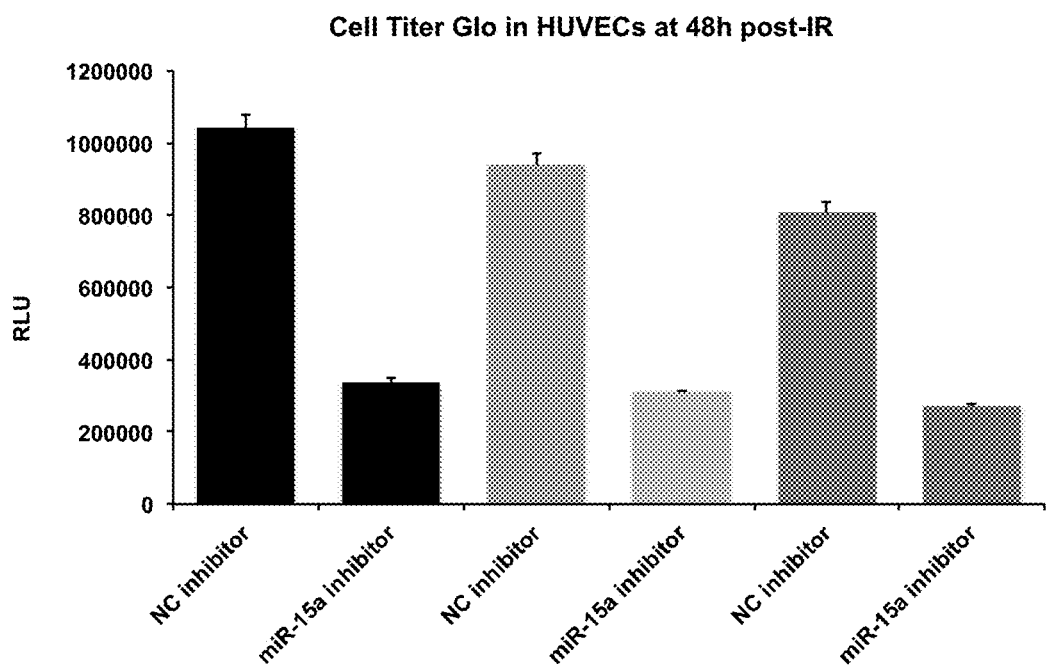
Figure 16B:
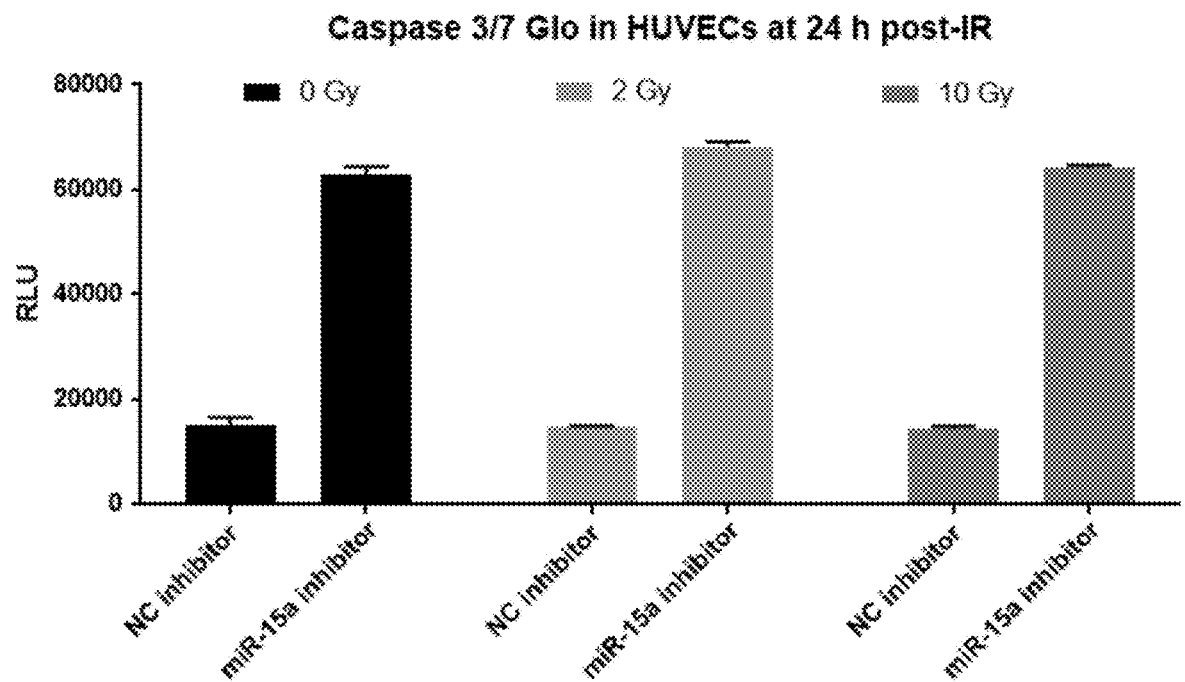

FIGS. 16A and 16B demonstrate HUVECs transfected with miR-15a inhibitor showed dramatically decreased cell proliferation at 48 h and increased Caspase activation 24 h post radiation.

Figure 17A:
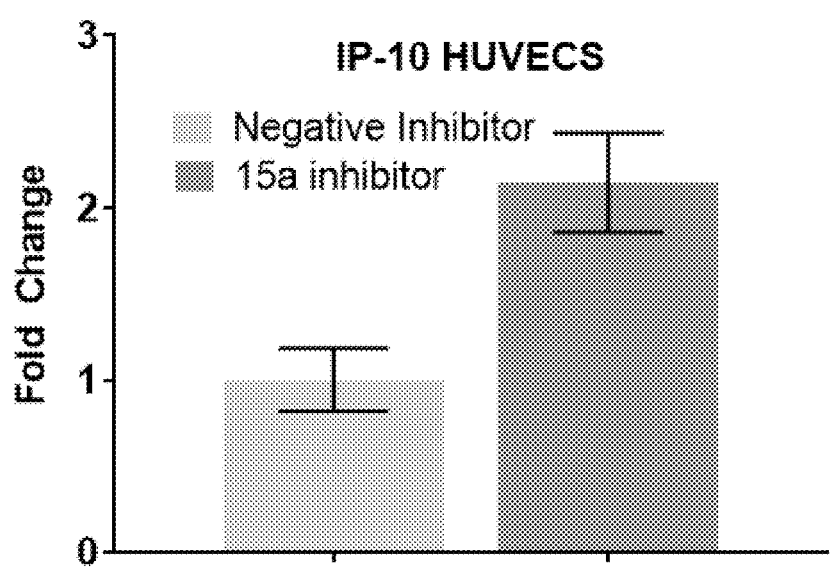
Figure 17B:
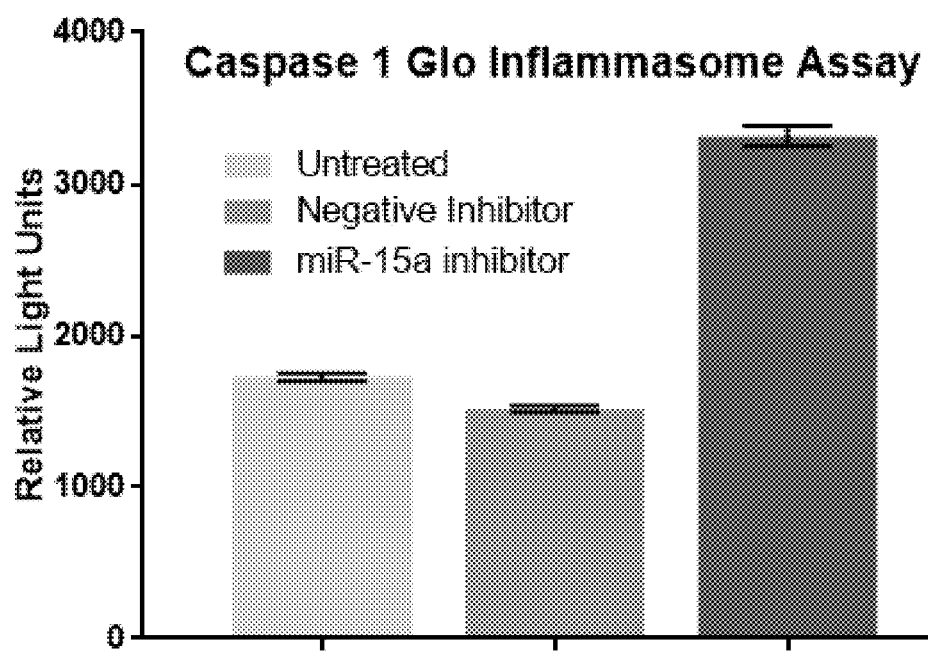
Figure 17C:
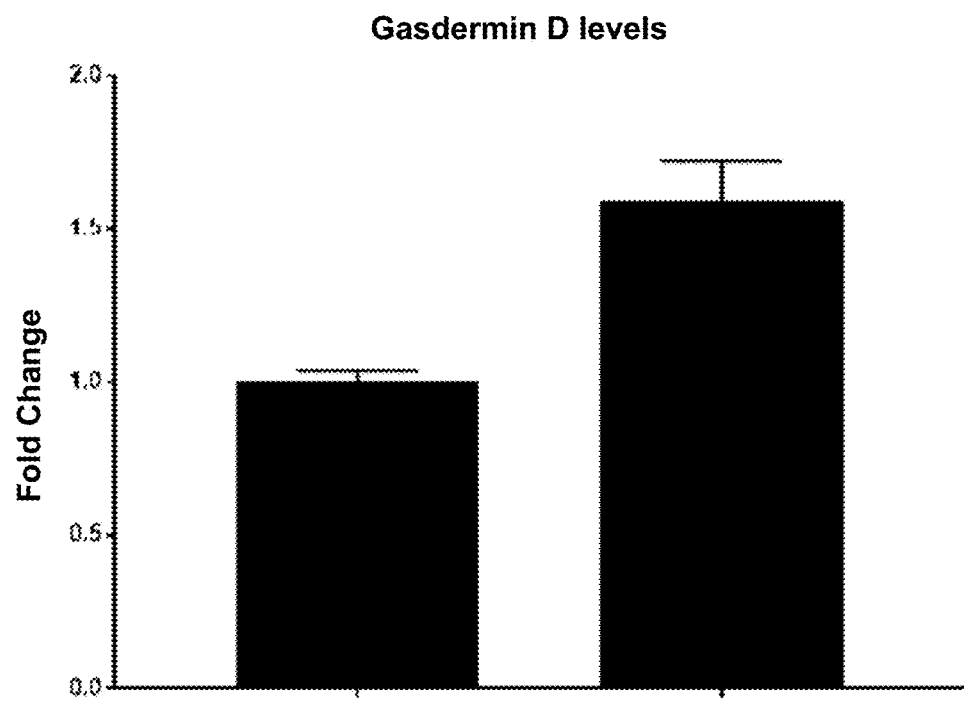

FIGS. 17A, 17B, and 17C demonstrate miR-15a inhibition affected inflammatory signaling in ECs by increasing IP10 (CXCL10) levels (FIG. 17A), enhancing caspase-1 inflammasome activation (FIG. 17B) and increasing the expression of Gasdermin D (FIG. 17C).

Figure 18A:
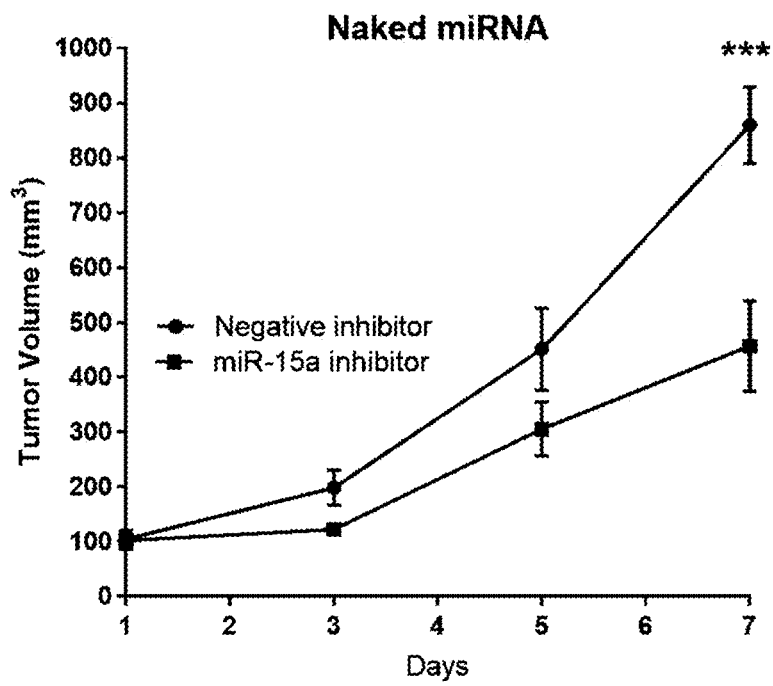
Figure 18B:
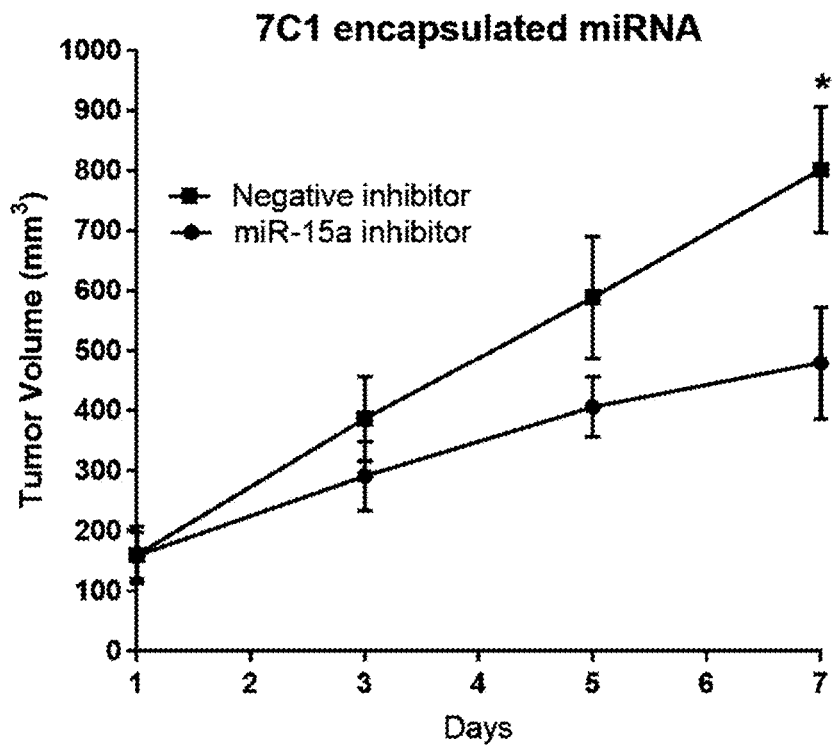
Figure 18C:
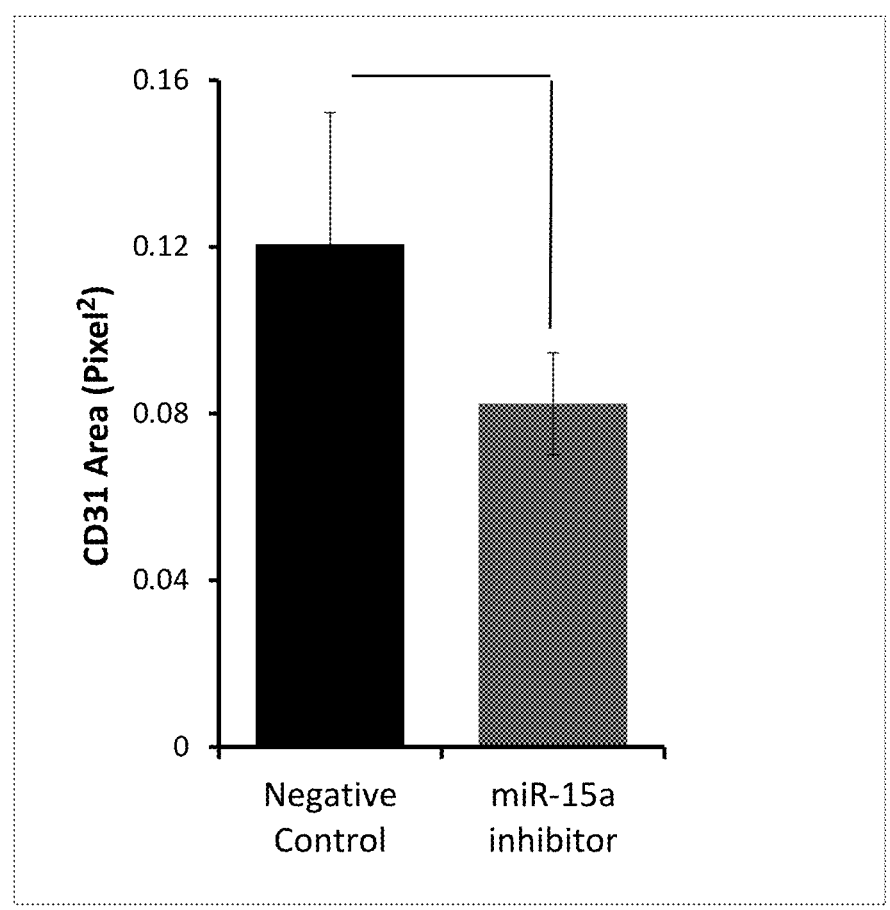

FIG. 18A and 18B illustrates effect of i.v. injected miR-15a inhibitor in a murine CT26 colorectal carcinoma flank tumor model for naked miRNA (FIG. 18A) and 7C1 encapsulated miRNA (FIG. 18B); and FIG. 18C describes quantification of tumor blood vessels as measured by staining tumor tissue sections from the indicated treatments groups for CD31 and a nuclear marker.

DETAILED DESCRIPTION

The term "microRNA", optionally abbreviated as miRNA or miR, as used herein is understood to be a small, non-coding RNA molecule functioning in RNA silencing and post-transcriptional gene expression regulation.

The abbreviation "Gy" herein is understood to indicate gray, the unit of ionizing radiation dose defined as the absorption of one joule of radiation per kilogram of matter.

The terms "therapeutically effective", "pharmaceutically effective" or "therapeutically/pharmaceutically effective" amounts refers to an amount that is sufficient to effect treatment, as defined below, when administered to a subject (e.g., a mammal, such as a human) in need of such treatment. The therapeutically or pharmaceutically effective amount will vary depending upon the subject and disease condition being treated, the weight and age of the subject, the severity of the disease condition, the manner of administration and the like, which can readily be determined by one of ordinary skill in the art.

"Treatment" or "treating" is an approach for obtaining beneficial or desired results including clinical results. Beneficial or desired clinical results may include one or more of the following: (i) inhibiting the disease or condition (e.g., decreasing one or more symptoms resulting from the disease or condition, and/or diminishing the extent of the disease or condition); (ii) slowing or arresting the development of one or more clinical symptoms associated with the disease or condition (e.g., stabilizing the disease or condition, preventing or delaying the worsening or progression of the disease or condition, and/or preventing or delaying the spread (e.g., metastasis) of the disease or condition); and/or (iii) relieving the disease, that is, causing the regression of clinical symptoms (e.g., ameliorating the disease state, providing partial or total remission of the disease or condition, enhancing effect of another medication, delaying the progression of the disease, increasing the quality of life, and/or prolonging survival). The terms "inhibiting" or "inhibition" indicates a decrease, such as a significant decrease, in the baseline activity of a biological activity or process.

Almost 50% or all cancer patients undergo some form of radiotherapy. However only half of these patients have significant responses to radiation. While several specific options exist to escalate the dose of radiation (e.g. stereotactic body radiation therapy, SBRT or stereotactic radiosurgery, SRS) while minimizing damage to normal organs, often this is not feasible due the location of tumor, organ site etc.) Therefore approaches to enhance the efficacy of lower (conventional dose radiation) are valuable. By "significant" is meant any detectable change that is statistically significant in a standard parametric test of statistical significance such as Student's T-test, where $p<0.05$.

"Delaying" the development of a disease or condition means to defer, hinder, slow, retard, stabilize, and/or postpone development of the disease or condition. This delay can be of varying lengths of time, depending on the history of the disease or condition, and/or subject being treated. A method that "delays" development of a disease or condition is a method that reduces probability of disease or condition development in a given timeframe and/or reduces the extent of the disease or condition in a given time frame, when compared to not using the method. Such comparisons are typically based on clinical studies, using a statistically significant number of subjects. Disease or condition development can be detectable using standard methods, such as routine physical exams, mammography, imaging, or biopsy. Development may also refer to disease or condition progression that may be initially undetectable and includes occurrence, recurrence, and onset.

The current disclosure provides that microRNA-15a inhibition achieves this effect. Without being bound by theory, the effect can be triggered in part by augmenting a cell death pathway in cancer blood vessels. The enzyme termed Acid sphingomyelinase (SMPD1) leads to the production of ceramide from endothelial cells. Ceramide is a potent inducer of cell death. While low dose radiation does not appreciably increase either SMPD1 levels or ceramide levels, higher doses enhance ceramide production and therefore increase endothelial and tumor cell death. This coincides with the fact that miR-15a levels increase at lower doses and decrease at higher doses. As shown herein, an miR-15a mimic is able to decrease the mRNA levels of the SMPD1 enzyme. It is also shown that miR-15a inhibition decreases cell proliferation, increases cell death in endothelial cells and in colorectal cancer cells (mouse and human) in vitro. Treatment of tumor bearing mice with an miR-15a inhibitor decreased tumor growth. Given that there are currently no therapeutic strategies to enhance enzyme function, miR-15a inhibition can mimic the effects of higher dose radiation and increase tumor and endothelial cell killing.

Particular embodiments include microRNA-15a inhibition as a radiation sensitizer. In particular embodiments microRNA-15a inhibition can be used in the treatment of cancers that respond to radiation but toxicity limits the use of radiation doses (e.g., such as locally delivered agent in brain tumors especially pediatric (radiation can decrease IQ in pediatric patients)). Other highly relevant tumor types include those that metastasize to liver and colorectal cancers.

microRNA-15a inhibition can also be considered as a biomarker for predicting efficacy of other radiation sensitizers/neoadjuvant treatments. Any therapy that shows a decrease in miR-15a levels can enhance cell killing and therefore offer better radiation therapy benefits.

As such, provided herein is a method of sensitizing a cancer cell to radiation comprising administering a microRNA-15a inhibitor.

Also provided is a method of treating a cancerous tumor in a human comprising administering a microRNA-15a inhibitor and radiation Also provided is a method of treating cancer in a human, the method comprising administering to a human in need thereof a pharmaceutically effective amount of an inhibitor of miR-15a.

Further provided is a method of treating cancer in a human, the method comprising administering to a human in need thereof a pharmaceutically effective amount of an inhibitor of miR-15a and a therapeutically effective amount of radiation.

Also provided is a method of enhancing the effect of radiation therapy in a human with a cancer, the method comprising administering to a human in need thereof a pharmaceutically effective amount of an inhibitor of miR-15a.

Additionally provided is a method of enhancing radiation-induced endothelial apoptosis in a human with cancer undergoing radiation therapy, the method comprising administering to a human in need thereof a pharmaceutically effective amount of an inhibitor of miR-15a.

In some embodiments, the cancer is selected from the group of esophageal cancer, stomach cancer, pancreatic cancer, kidney skin, skin cancer, and liver cancer. In other embodiments, the cancer is a lung cancer selected from the group of non-small cell lung cancer (including squamous cell carcinoma, adenocarcinoma, and large cell carcinoma), Small Cell Lung Cancer, Lung Carcinoid Tumor, and metastatic breast cancer. In other embodiments, the cancer is a lung cancer selected from the group of non-small cell lung cancer (including squamous cell carcinoma, adenocarcinoma, and large cell carcinoma), Small Cell Lung Cancer, Lung Carcinoid Tumor, and metastatic breast cancer.

In further embodiments, the cancer is a lung cancer selected from the group of non-small cell lung cancer (including squamous cell carcinoma, adenocarcinoma, and large cell carcinoma), Small Cell Lung Cancer, Lung Carcinoid Tumor, and metastatic breast cancer.

In different embodiments, the cancer is a colorectal cancer selected from the group of adenocarcinomas, gastrointestinal carcinoid tumors, primary colorectal lymphomas, and metastatic colorectal cancers.

In some embodiments, the cancer is a breast cancer selected from the group of ductal carcinoma in situ, invasive ductal carcinoma (including the IDC types: medullary carcinoma of the breast, mucinous carcinoma of the breast, papillary carcinoma of the breast, cribriform carcinoma of the breast) invasive lobular carcinoma, inflammatory breast cancer, lobular carcinoma in situ, male breast cancer, Luminal A breast cancer, Luminal B breast cancer, Triple-Negative/Basa-like breast cancer, HER2-enriched breast cancer, Normal-like breast cancer, Paget's disease of the nipple, Phyllodes tumors of the breast, and metastatic breast cancer.

In additional embodiments the cancer is an esophageal cancer selected from the group of adenocarcinoma, squamous cell carcinoma, small cell carcinoma, sarcoma, lymphoma, melanoma, choriocarcinoma, and metastatic esophageal cancers. In other embodiments the cancer is a stomach cancer selected from the group of adenocarcinoma, lymphoma, gastrointestinal stromal tumor (GIST), carcinoid tumor, squamous cell carcinoma, small cell carcinoma, leiomyosarcoma, and metastatic stomach cancers.

In more embodiments the cancer is a) an exocrine pancreatic cancer selected from the group of adenocarcinoma, Acinar cell carcinoma, intraductal papillary-mucinous neoplasm, solid pseudopapillary neoplasms, pancreatoblastoma, and mucinous cystadenocarcinoma; or b) an endocrine pancreatic cancer selected from the group of gastrinoma, glucagonoma, insulinoma, somatostatinoma, and VIPoma (Verner-Morrison syndrome).

In separate embodiments, the cancer is a pancreatic cancer selected from the group of nonfunctional islet cell tumor, Multiple Endocrine Neoplasia Type-1 (MEN1), and metastatic pancreatic cancers. In others, the cancer is a kidney cancer selected from the group of renal cell carcinoma, urothelial carcinoma, sarcoma, Wilms tumor, and lymphoma. In still other embodiments the cancer is a kidney cancer selected from the group of clear cell cancers, papillary kidney cancers, sarcomatoid features cancers, medullary/collecting duct cancers, chromophobe cancers, oncocytomas, angiomyolipomas, and metastatic kidney cancers.

In different embodiments the cancer is a skin cancer selected from the group of actinic keratoses, basal cell carcinoma, squamous cell carcinoma, melanoma, and metastatic skin cancers.

Additional embodiments comprise those in which the cancer is a primary liver cancer. In some embodiments the primary liver cancer may be selected from the group of bile duct cancer (cholangiocarcinoma), Fibrolamellar hepatocellular cancer, Hemangiosarcomas, Angiosarcomas, Hepatoblastomas, and metastatic primary liver cancers.

In additional embodiments, the cancer is a secondary liver cancer. In further embodiments the secondary liver cancer is selected from the group of lung cancer, colorectal cancer, esophageal cancer, stomach cancer, pancreatic cancer, kidney cancer, and skin cancer.

In different embodiments herein, the radiation therapy utilized may comprise different individual doses of radiation and lengths of radiation regimen which will be determined by medical professionals. In some embodiments, the radiation will be individually selected from the group of ranges of 0.5-5 gray (Gy), 0.5-3 Gy, 0.5-2 Gy, 0.5-1.5 Gy, 1-5 Gy, 1.5-5 Gy, 2-5 Gy, 3-5 Gy, 1-3 Gy, 1-2 Gy, 5-10 Gy, 10-15 Gy, and 15-20 Gy. Other independent radiation doses may be selected from the group of 0.5 Gy, 1 Gy, 1.5 Gy, 2 Gy, 2.5 Gy, 3 Gy, 4 Gy, 5 Gy, 6 Gy, 7 Gy, 8 Gy, 9 Gy, 10 Gy, 11 Gy, 12 Gy, 13 Gy, 14 Gy, 15 Gy, 16 Gy, 17 Gy, 18 Gy, 19 Gy, and 20 Gy.

Also provided is the use of an miR-15a inhibitor as described herein in the preparation of a medicament for the treatment of one or more of the cancers described herein.

Any method of inhibiting microRNA-15a can be used. Particular embodiments can utilize the oligonucleotide (CACAAACCAUUAUGUGCUGCUA (SEQ ID NO: 1)) that is perfectly complementary to endogenous human miR-15a. The human and mouse sequences are highly similar and SEQ ID NO: 1 Is predicted to inhibit both. SEQ ID NO: 1 can be obtained commercially from Exiqon and IDT. In particular embodiments, SEQ ID NO: 1 backbone modifications include phosphorothioate to stabilize and prevent degradation and a 2' modification of the ribose sugar (typically O-Me and sometimes F-Me). Variants of SEQ ID NO: 1 with at least 90% sequence identity may also be used so long as there is no statistically-significant degradation of effect as measured by an experimental protocol described herein.

Truncated sequences which may also be used in the methods described herein include:

| Length | Sequence | Corresponding positions in SEQ ID NO: 1 |
|---|---|---|
| 15-mers | CACAAACCAUUAUGU | 1-15 |
| | ACAAACCAUUAUGUG | 2-16 |
| | CAAACCAUUAUGUGC | 3-17 |
| | AAACCAUUAUGUGCU | 4-18 |
| | AACCAUUAUGUGCUG | 5-19 |
| | ACCAUUAUGUGCUGC | 6-20 |
| | CCAUUAUGUGCUGCU | 7-21 |
| | CAUUAUGUGCUGCUA | 8-22 |
| 14-mers | CACAAACCAUUAUG | 1-14 |
| | ACAAACCAUUAUGU | 2-15 |
| | CAAACCAUUAUGUG | 3-16 |
| | AAACCAUUAUGUGC | 4-17 |
| | AACCAUUAUGUGCU | 5-18 |
| | ACCAUUAUGUGCUG | 6-19 |
| | CCAUUAUGUGCUGC | 7-20 |
| | CAUUAUGUGCUGCU | 8-21 |
| | AUUAUGUGCUGCUA | 9-22 |
| 13-mers | CACAAACCAUUAU | 1-13 |
| | ACAAACCAUUAUG | 2-14 |
| | CAAACCAUUAUGU | 3-15 |
| | AAACCAUUAUGUG | 4-16 |
| | AACCAUUAUGUGC | 5-17 |
| | ACCAUUAUGUGCU | 6-18 |
| | CCAUUAUGUGCUG | 7-19 |
| | CAUUAUGUGCUGC | 8-20 |
| | AUUAUGUGCUGCU | 9-21 |
| | UUAUGUGCUGCUA | 10-22 |
| 12-mers | CACAAACCAUUA | 1-12 |
| | ACAAACCAUUAU | 2-13 |
| | CAAACCAUUAUG | 3-14 |
| | AAACCAUUAUGU | 4-15 |
| | AACCAUUAUGUG | 5-16 |
| | ACCAUUAUGUGC | 6-17 |
| | CCAUUAUGUGCU | 7-18 |
| | CAUUAUGUGCUG | 8-19 |
| | AUUAUGUGCUGC | 9-20 |
| | UUAUGUGCUGCU | 10-21 |
| | UAUGUGCUGCUA | 11-22 |
| 11-mers | CACAAACCAUU | 1-11 |
| | ACAAACCAUUA | 2-12 |
| | CAAACCAUUAU | 3-13 |
| | AAACCAUUAUG | 4-14 |
| | AACCAUUAUGU | 5-15 |
| | ACCAUUAUGUG | 6-16 |
| | CCAUUAUGUGC | 7-17 |
| | CAUUAUGUGCU | 8-18 |
| | AUUAUGUGCUG | 9-20 |
| | UUAUGUGCUGC | 10-20 |
| | UAUGUGCUGCU | 11-21 |
| | AUGUGCUGCUA | 12-22 |
| 10-mers | CACAAACCAU | 1-10 |
| | ACAAACCAUU | 2-11 |
| | CAAACCAUUA | 3-12 |
| | AAACCAUUAU | 4-13 |
| | AACCAUUAUG | 5-14 |
| | ACCAUUAUGU | 6-15 |
| | CCAUUAUGUG | 7-16 |
| | CAUUAUGUGC | 8-17 |
| | AUUAUGUGCU | 9-18 |
| | UUAUGUGCUG | 10-19 |
| | UAUGUGCUGC | 11-20 |
| | AUGUGCUGCU | 12-21 |
| | UGUGCUGCUA | 13-22 |
| 9-mers | CACAAACCA | 1-9 |
| | ACAAACCAU | 2-10 |
| | CAAACCAUU | 3-11 |
| | AAACCAUUA | 4-12 |
| | AACCAUUAU | 5-13 |
| | ACCAUUAUG | 6-14 |
| | CCAUUAUGU | 7-15 |
| | CAUUAUGUG | 8-16 |
| | AUUAUGUGC | 9-17 |
| | UUAUGUGCU | 10-18 |
| | UAUGUGCUG | 11-19 |
| | AUGUGCUGC | 12-20 |
| | UGUGCUGCU | 13-21 |
| | GUGCUGCUA | 14-22 |

"% sequence identity" refers to a relationship between two or more sequences, as determined by comparing the sequences. In the art, "identity" also means the degree of sequence relatedness between protein and nucleic acid sequences as determined by the match between strings of such sequences. "Identity" (often referred to as "similarity") can be readily calculated by known methods, including those described in: Computational Molecular Biology (Lesk, A. M., ed.) Oxford University Press, N Y (1988); Biocomputing: Informatics and Genome Projects (Smith, D. W., ed.) Academic Press, N Y (1994); Computer Analysis of Sequence Data, Part I (Griffin, A. M., and Griffin, H. G., eds.) Humana Press, N J (1994); Sequence Analysis in Molecular Biology (Von Heijne, G., ed.) Academic Press (1987); and Sequence Analysis Primer (Gribskov, M. and Devereux, J., eds.) Oxford University Press, NY (1992). Preferred methods to determine identity are designed to give the best match between the sequences tested. Methods to determine identity and similarity are codified in publicly available computer programs. Sequence alignments and percent identity calculations may be performed using the Megalign program of the LASERGENE bioinformatics computing suite (DNASTAR, Inc., Madison, Wis.). Multiple alignment of the sequences can also be performed using the Clustal method of alignment (Higgins and Sharp CABIOS, 5, 151-153 (1989) with default parameters (GAP PENALTY=10, GAP LENGTH PENALTY=10). Relevant programs also include the GCG suite of programs (Wisconsin Package Version 9.0, Genetics Computer Group (GCG), Madison, Wis.); BLASTP, BLASTN, BLASTX (Altschul, et al., J. Mol. Biol. 215:403-410 (1990); DNASTAR (DNASTAR, Inc., Madison, Wis.); and the FASTA program incorporating the Smith-Waterman algorithm (Pearson, Comput. Methods Genome Res., [Proc. Int. Symp.] (1994), Meeting Date 1992, 111-20. Editor(s): Suhai, Sandor. Publisher: Plenum, New York, N.Y. Within the context of this disclosure it will be understood that where sequence analysis software is used for analysis, the results of the analysis are based on the "default values" of the program referenced. "Default values" will mean any set of values or parameters, which originally load with the software when first initialized.

microRNA-15a inhibitors can be formulated into compositions for administration to subjects. Exemplary generally used pharmaceutically acceptable carriers include absorption delaying agents, antioxidants, binders, buffering agents, bulking agents or fillers, chelating agents, coatings, disintegration agents, dispersion media, gels, isotonic agents, lubricants, preservatives, salts, solvents or co-solvents, stabilizers, surfactants, and/or delivery vehicles.

The compositions can be formulated for administration by, for example, injection, inhalation, infusion, perfusion, lavage, or ingestion. For injection, compositions can be formulated as aqueous solutions, such as in buffers including Hanks' solution, Ringer's solution, or physiological saline. For oral administration, the compositions can be formulated as tablets, pills, dragees, capsules, liquids, gels, syrups, slurries, suspensions and the like.

While the miRNA segments herein may be administered systemically, localized concentrations may be better maintained by intratumoral injection or other local administration with or without carriers, including intracranial administrations.

MicroRNA segments may be delivered in oleic acid-based lipid nanoparticle formulations (Wang et al., J. Control Release, 2013 Dec. 28; 172(3); pp. 690-698), conjugated to cyclic arginine-glycine-aspartic acid (cRGD) peptides (He et al., Drug Delivery, 2017, 24(1): pp. 471-481), or bound to low molecular weight polyamine and lipid polymeric nanoparticles (Dahlman et al., Nat. Nanotechnol. 2014 August; 9(8): pp. 648-655). MicroRNAs can also be delivered using locked nucleic acids (LNAs), 2'-O-methyl oligonucleotides (such as antagomiRs), and peptide nucleic acids (PNAs) or nanoencapsulated PNAs (Cheng et al., Nature, February 2015, Vol. 518: pp. 107-112). Formulations may also be delivered through infusion, including the use of a hepatic arterial fusion pump to treat cancers of the liver, including metastatic cancers, including colon cancer (Zarour et al., Cellular and Molecular Gastroenterology and Hepatology, Vol. 3, No. 2, March 2017, pp. 163-173).

Any composition disclosed herein can advantageously include any other pharmaceutically acceptable carriers which include those that do not produce significantly adverse, allergic, or other untoward reactions that outweigh the benefit of administration. Exemplary pharmaceutically acceptable carriers and formulations are disclosed in Remington's Pharmaceutical Sciences, 18th Ed. Mack Printing Company, 1990. Moreover, formulations can be prepared to meet sterility, pyrogenicity, general safety, and purity standards as required by U.S. FDA Office of Biological Standards and/or other relevant foreign regulatory agencies.

While the miRNA segments herein may be administered systemically, localized concentrations may be better maintained by intratumoral injection or other local administration with or without carriers, including intracranial administrations.

MicroRNA segments may be delivered in oleic acid-based lipid nanoparticle formulations (Wang et al., J. Control Release, 2013 Dec. 28; 172(3); pp. 690-698), conjugated to cyclic arginine-glycine-aspartic acid (cRGD) peptides (He et al., Drug Delivery, 2017, 24(1): pp. 471-481), or bound to low molecular weight polyamine and lipid polymeric nanoparticles (Dahlman et al., Nat. Nanotechnol. 2014 August; 9(8): pp. 648-655). MicroRNAs can also be delivered using locked nucleic acids (LNAs), 2'-O-methyl oligonucleotides (such as antagomiRs), and peptide nucleic acids (PNAs) or nanoencapsulated PNAs (Cheng et al., Nature, February 2015, Vol. 518: pp. 107-112). Formulations may also be delivered through infusion, including the use of a hepatic arterial fusion pump to treat cancers of the liver, including metastatic cancers, including colon cancer (Zarour et al., Cellular and Molecular Gastroenterology and Hepatology, Vol. 3, No. 2, March 2017, pp. 163-173).

Hepatic arterial infusion, also known as hepatic artery chemo-infusion (HAI), may be used as a contained local administration of miR-15a inhibitors for the treatment of primary and secondary liver cancers, including metastases of lung, colorectal, breast, esophagus, stomach, pancreas, kidneys, and skin cancers. Commercially available hepatic arterial infusion pumps may be used for such administrations, including the Medtronic SynchroMed® and IsoMed® infusion systems available from Medtronic, Inc. and the CODMAN® 3000 HAI pump available from Codman, a Johnson & Johnson company.

Methods disclosed herein include treating subjects (humans, veterinary animals (dogs, cats, reptiles, birds, etc.) livestock (horses, cattle, goats, pigs, chickens, etc.) and research animals (monkeys, rats, mice, fish, etc.) with compositions disclosed herein. Treating subjects includes delivering therapeutically effective amounts. Therapeutically effective amounts include those that provide effective amounts, prophylactic treatments and/or therapeutic treatments.

An "effective amount" is the amount of a composition necessary to result in a desired physiological change in the subject. Effective amounts are often administered for research purposes. Effective amounts disclosed herein can cause a statistically-significant effect in an animal model or in vitro assay relevant to the assessment of a cancer's development or progression.

A "prophylactic treatment" includes a treatment administered to a subject who does not display signs or symptoms of a cancer or displays only early signs or symptoms of a cancer such that treatment is administered for the purpose of diminishing or decreasing the risk of developing the cancer further. Thus, a prophylactic treatment functions as a preventative treatment against a cancer. In particular embodiments, prophylactic treatments reduce, delay, or prevent metastasis from a primary a cancer tumor site from occurring.

A "therapeutic treatment" includes a treatment administered to a subject who displays symptoms or signs of a cancer and is administered to the subject for the purpose of diminishing or eliminating those signs or symptoms of the cancer. The therapeutic treatment can reduce, control, or eliminate the presence or activity of the cancer and/or reduce control or eliminate side effects of the cancer.

Function as an effective amount, prophylactic treatment or therapeutic treatment are not mutually exclusive, and in particular embodiments, administered dosages may accomplish more than one treatment type.

In particular embodiments, therapeutically/pharmaceutically effective or pharmaceutically effective amounts provide anti-cancer effects. Anti-cancer effects include a decrease in the number of cancer cells, decrease in the number of metastases, a decrease in tumor volume, an increase in life expectancy, induced chemo- or radiosensitivity in cancer cells, inhibited angiogenesis near cancer cells, inhibited cancer cell proliferation, inhibited tumor growth, prevented or reduced metastases, prolonged subject life, reduced cancer-associated pain, increased sensitivity to low dose radiation and/or reduced relapse or re-occurrence of cancer following treatment.

For administration, therapeutically/pharmaceutically effective or pharmaceutically effective amounts (also referred to herein as doses) can be initially estimated based on results from in vitro assays and/or animal model studies. Such information can be used to more accurately determine useful doses in subjects of interest. The actual dose amount administered to a particular subject can be determined by a physician, veterinarian or researcher taking into account parameters such as physical and physiological factors including target, body weight, severity of condition, type of cancer, stage of cancer, previous or concurrent therapeutic interventions, idiopathy of the subject and route of administration.

Useful doses can range from 0.1 to 5 µg/kg or from 0.5 to 1 µg/kg. In other examples, a dose can include 1 µg/kg, 15 µg/kg, 30 µg/kg, 50 µg/kg, 55 µg/kg, 70 µg/kg, 90 µg/kg, 150 µg/kg, 350 µg/kg, 500 µg/kg, 750 µg/kg, 1000 µg/kg, 0.1 to 5 mg/kg or from 0.5 to 1 mg/kg. In other a dose can include 1 mg/kg, 10 mg/kg, 30 mg/kg, 50 mg/kg, 70 mg/kg, 100 mg/kg, 300 mg/kg, 500 mg/kg, 700 mg/kg, 1000 mg/kg or more.

Therapeutically/pharmaceutically effective amounts can be achieved by administering single or multiple doses during the course of a treatment regimen.

Figure 1:
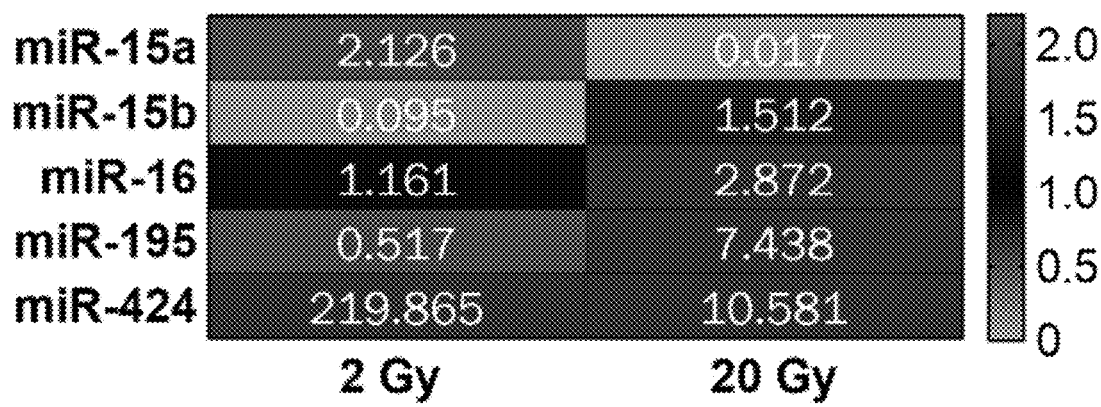
FIG. 1. miRs exhibit radiation dose-dependent differential expression. miRNA candidates targeting SMPD1 exhibit radiation dose-dependent differential expression at 6 h post-IR. Fold changes are indicated in by cell shading relative to expression of the respective miRNA in non-irradiated samples.
Figure 1:
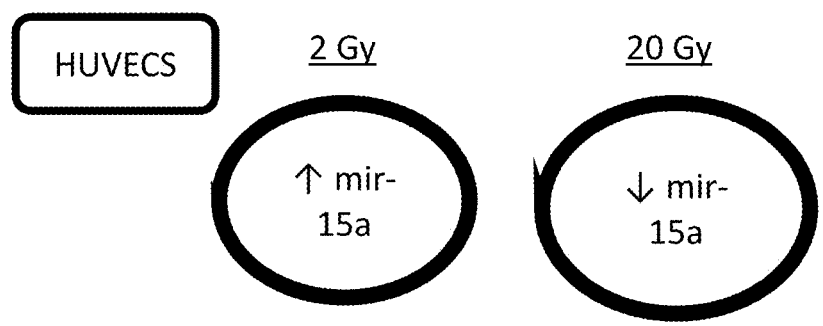

Example 1. miRs dysregulated in human umbilical vein endothelial cells (HUVECs) were profiled to ascertain the effect of radiation dose magnitude on angiogenesis. HUVECs were treated either a single 2 Gy or 20 Gy dose via Cs-137. miR-15a exhibited the greatest differential change at 6 hours post-IR between exposure of 2 Gy and 20 Gy radiation relative to non-irradiated samples (FIG. 1). Using miR target prediction bioinformatics platforms, distinct miRs proposed as targeting SMPD1 [Metheetrairut, C. and F. J. Slack, MicroRNAs in the ionizing radiation response and in radiotherapy. Curr Opin Genet Dev, 2013.23(1): p. 12-9] including miR-15a were identified. Subsequent quantitation via PCR was performed which confirmed increased miR-15a expression at conventional dose radiation and decreased expression at ablative doses (Data not shown). To confirm the regulation of SMPD1 by miR-15a gain of function studies with miR-15a mimics were performed. That transfection of miR-15a significantly reduced expression of SMPD1 mRNA levels was first confirmed (FIG. 2).

Cell Titer Glo® (Promega) was utilized to measure cell viability in HUVECs transfected with exogenous miR-15a mimic and compared to a negative control scrambled miR counterpart. At 24 hours post-transfection, these cells were further subdivided and received sham irradiation, 2 Gy, or 10 Gy. Cells transfected with miR-15a inhibitor demonstrated dramatically decreased cell viability 48 hours post IR at a level lower than either dose of radiation alone (FIG. 3; upper panel). Interestingly, Caspase Glo® activity, which provides a measure of apoptosis, demonstrated distinct upregulation of caspase activity with HUVECS treated with combination of miR-15a inhibitor and radiation (FIG. 3; lower panel).

While noting SMPD1 is characterized by a 20 fold increased expression in endothelial cells relative to other cell types [Wright, et al., *microRNAs: The Short Link between Cancer and RT-Induced DNA* Front Oncol, 2014. 4: p. 133], the effects of miR-15a inhibitor was analyzed on apoptosis in a similar fashion in malignant cell lines focusing on colorectal cell lines. Traditionally, colorectal cancer is treated with neoadjuvant chemoradiation using large fields, which encompass the primary tumor and a large extent of potential microscopic disease [Wang, B. L., et al., *The therapeutic and adverse effects of modified radiation fields for patients with rectal cancer*. Clin Colorectal Cancer, 2012. 11(4): p. 255-62]. The extent of radiation coverage abrogates the use of high dose per fraction SBRT or SRS as it would confer considerable toxicity to normal adjacent structures. Insights into dose-specific miR differences including miR-15a and their associated regulatory pathways could enhance treatment of this disease site limited to lower RT doses through alternative or concurrent interventions which could elicit miR regulatory nodes associated with the differentially expressed miR. CT26 colorectal cancer cells were transfected and irradiated as described for HUVECs above. Similar to HUVECs, miR-15a inhibitor dramatically decreased cell viability. The cell line was selected to transition to syngeneic murine hindlimb implantation models in to BALB/c mice. FIG. 4; upper panel).

The first in vivo assay implemented CT26 cells implanted into the hindlimb Matrigel® bioscaffolding matrix. Upon tumor growth to 100 cm$^3$, mice (n=10) was equally subdivided to receive either 1) Negative control scramble miR inhibitor or 2) miR-15a inhibitor. The miR inhibitors were administered via tail vein injection on days 0, 2, 4, and 6. Tumors were measured daily for 7 days. Treatment with miR-15a inhibitor resulted in a 50% decrease in tumor growth after 7 days (FIG. 4; lower panel).

As will be understood by one of ordinary skill in the art, each embodiment disclosed herein can comprise, consist essentially of or consist of its particular stated element, step, ingredient or component. Thus, the terms "include" or "including" should be interpreted to recite: "comprise, consist of, or consist essentially of." The transition term "comprise" or "comprises" means includes, but is not limited to, and allows for the inclusion of unspecified elements, steps, ingredients, or components, even in major amounts. The transitional phrase "consisting of" excludes any element, step, ingredient or component not specified. The transition phrase "consisting essentially of" limits the scope of the embodiment to the specified elements, steps, ingredients or components and to those that do not materially affect the embodiment. A material effect would cause a statistically-significant reduction in increased sensitivity to low dose radiation, as described herein.

Unless otherwise indicated, all numbers expressing quantities of ingredients, properties such as molecular weight, reaction conditions, and so forth used in the specification and claims are to be understood as being modified in all instances by the term "about." Accordingly, unless indicated to the contrary, the numerical parameters set forth in the specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques. When further clarity is required, the term "about" has the meaning reasonably ascribed to it by a person skilled in the art when used in conjunction with a stated numerical value or range, i.e. denoting somewhat more or somewhat less than the stated value or range, to within a range of ±20% of the stated value; ±19% of the stated value; ±18% of the stated value; ±17% of the stated value; ±16% of the stated value; ±15% of the stated value; ±14% of the stated value; ±13% of the stated value; ±12% of the stated value; ±11% of the stated value; ±10% of the stated value; ±9% of the stated value; ±8% of the stated value; ±7% of the stated value; ±6% of the stated value; ±5% of the stated value; ±4% of the stated value; ±3% of the stated value; ±2% of the stated value; or ±1% of the stated value.

Notwithstanding that the numerical ranges and parameters setting forth the broad scope of the invention are approximations, the numerical values set forth in the specific examples are reported as precisely as possible. Any numerical value, however, inherently contains certain errors necessarily resulting from the standard deviation found in their respective testing measurements.

The terms "a," "an," "the" and similar referents used in the context of describing the invention (especially in the context of the following claims) are to be construed to cover both the singular and the plural, unless otherwise indicated herein or clearly contradicted by context. Recitation of ranges of values herein is merely intended to serve as a shorthand method of referring individually to each separate value falling within the range. Unless otherwise indicated herein, each individual value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein is intended merely to better illuminate the invention and does not pose a limitation on the scope of the invention otherwise claimed. No language in the specification should be construed as indicating any non-claimed element essential to the practice of the invention.

Groupings of alternative elements or embodiments of the invention disclosed herein are not to be construed as limitations. Each group member may be referred to and claimed individually or in any combination with other members of the group or other elements found herein. It is anticipated that one or more members of a group may be included in, or deleted from, a group for reasons of convenience and/or patentability. When any such inclusion or deletion occurs, the specification is deemed to contain the group as modified thus fulfilling the written description of all Markush groups used in the appended claims.

Certain embodiments of this invention are described herein, including the best mode known to the inventors for carrying out the invention. Of course, variations on these described embodiments will become apparent to those of ordinary skill in the art upon reading the foregoing description. The inventor expects skilled artisans to employ such variations as appropriate, and the inventors intend for the invention to be practiced otherwise than specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

Furthermore, numerous references have been made to patents, printed publications, journal articles and other written text throughout this specification (referenced materials herein). Each of the referenced materials are individually incorporated herein by reference in their entirety for their referenced teaching.

In closing, it is to be understood that the embodiments of the invention disclosed herein are illustrative of the principles of the present invention. Other modifications that may be employed are within the scope of the invention. Thus, by way of example, but not of limitation, alternative configurations of the present invention may be utilized in accordance with the teachings herein. Accordingly, the present invention is not limited to that precisely as shown and described.

The particulars shown herein are by way of example and for purposes of illustrative discussion of the preferred embodiments of the present invention only and are presented in the cause of providing what is believed to be the most useful and readily understood description of the principles and conceptual aspects of various embodiments of the invention. In this regard, no attempt is made to show structural details of the invention in more detail than is necessary for the fundamental understanding of the invention, the description taken with the drawings and/or examples making apparent to those skilled in the art how the several forms of the invention may be embodied in practice.

Definitions and explanations used in the present disclosure are meant and intended to be controlling in any future construction unless clearly and unambiguously modified in the following examples or when application of the meaning renders any construction meaningless or essentially meaningless. In cases where the construction of the term would render it meaningless or essentially meaningless, the definition should be taken from Webster's Dictionary, 3rd Edition or a dictionary known to those of ordinary skill in the art, such as the Oxford Dictionary of Biochemistry and Molecular Biology (Ed. Anthony Smith, Oxford University Press, Oxford, 2004).

Technological advances such as stereotactic body radiation therapy (SBRT) and stereotactic radiosurgery (SRS) have allowed significant improvements in therapeutic radiation dose escalation. These treatment modalities are able to ablate malignant tissue for excellent local control, however they cannot treat all disease sites due to toxicity concerns (Yu et al., Pract Radiat Oncol. 2015 May-June; 5(3):193-6; Trakul et al., Semin Radiat Oncol. 2014 April; 24(2):140-7; Dobbelstein et al., Nat Rev Drug Discov. 2015 June; 14(6): 405-23; Schaue et al., Nat Rev Clin Oncol. 2015 September; 12(9):527-40; and Bernier et al., Nat Rev Cancer. 2004 September; 4(9):737-47). Dose escalation augments DNA damage but also involves a vast number of tumor microenvironment (TME) regulators (Barker et al., Nat Rev Cancer. 2015 July; 15(7):409-25). Within the TME, high dose radiation modulates the adjacent vasculature, stroma, and immune cells to contribute to the ionizing radiation (IR) response (Timmerman et al., J Clin Oncol. 2014 Sep. 10; 32(26):2847-54). Radiation elicits endothelial cell dysfunction characterized by associated increased permeability, detachment from the underlying basement membrane, and apoptosis et al., Exp Cell Res. 1998 Jan. 10; 238(1):148-54; and Langley et al., Br J Cancer. 1997; 75(5):666-72). At ablative doses, greater than 8 Gy, there is rapid induction of sphingomyelinase-mediated production of ceramide, which triggers rapid onset of endothelial apoptosis (Garcia-Barros et al., Science. 2003 May 16; 300(5622):1155-9). Indeed, it is thought that endothelial apoptosis dictates the radiosensitivity of tumors. IR-mediated cell death combined with a pro-inflammatory state contributes to an immunostimulatory profile leading to further immunogenic cell death (ICD) (Gupta et al., J Immunol. 2012 Jul. 15; 189(2):558-66; and Krysko et al., Cancer. 2012 December; 12(12):860-75).

MiRs play an important role in radiation responses of both malignant cells and the TME (Mao et al., DNA and cell biology. 2014 October; 33(10):667-79; and Kraemer et al., Radiation research. 2011 November; 176(5):575-86). miRs are endogenous, short non-coding, single-stranded RNA spanning approximately 22 nucleotides. It has been shown that radiation-regulated miRs alter DNA damage repair pathways, pro-survival signaling pathways, cell-cycle checkpoint regulation, and apoptosis; functions which radiation therapy exploits for therapeutic gain (Czochor et al., Antioxid Redox Signal. 2014 Jul. 10; 21(2):293-3129-24; Gandellini et al., Trends Mol Med. 2014 September; 20(9): 529-39; Metheetrairut et al., Curr Opin Genet Dev. 2013 February; 23(1):12-9; Wright et al., Front Oncol. 2014; 4:133; Wilson et al., Nat Commun. 2016 Nov. 25; 7:13597; and Kelley et al., Annals of Surgery. 2017; 266(4):610-6). Previous work identified a group of miRs regulated in the tumor vasculature in response to radiation (Wilson et al., Nature Communications. 2016 11/25/online; 7:13597). In particular, we have observed that some miRs in ECs are differentially regulated in response to different doses of radiation. We focused further attention on miRs predicted to target SMPD1. We found miR-15a expressed the greatest magnitude difference between standard and ablative dose radiation with substantially lower miR-15a levels at higher doses. Our studies show that miR-15a targets SMPD1 in ECs and inhibition of miR-15a decreases EC and tumor cell proliferation, enhances cell death and diminishes tumor growth in a mouse CT26 colorectal carcinoma flank tumor model. Vascular-targeted nanoparticle delivery of miR-15a inhibitor is sufficient to both decrease tumor growth and angiogenesis. Consistent with the immunostimulatory role of miR-15a deficiency in autoimmune and infectious settings (Liu et al., Clinical Immunology, 2016; 164:106-13; and Moon et al., J Immunology. 2014; 193(9):4558-67), we found miR-15a inhibition increased CXCL10 expression and caspase-1 activation. In summary, our findings establish a new miR based regulatory pathway that affects SMPD1 and therefore vascular cell death in response to radiation dose. Inhibition of this pathway may mimic features of high dose radiation and therefore offers avenues for the development of targeted therapeutics.

Materials and Methods miRNA Profiling

RNA was extracted from HUVECs at 6 h post radiation with either 2 Gy or 20 Gy and miRs were profiled using TaqMan TLDA panels for human microRNAs. miRs proposed to target miR-15a as predicted by TargetScan were further analyzed. Mean fold change after normalization to housekeeping RNA, RNU48, is depicted.

Cell Culture and Reagents

HUVECs (Lonza) were cultured in EBM-2 media (Lonza) supplemented with 10% fetal calf serum (Hyclone). CT-26 cells (ATCC) were culture in RPMI media supplement with 10% fetal calf serum and antibiotics. HCT-116 cells (ATCC) were cultured in McCoy's supplemented with 10% Fetal Calf Serum and antibiotics. Cells were tested and found negative for mycoplasma contamination before use in the assays described.

Transfections

Cells were reverse transfected with miR-15a-5p mimics, inhibitors and their respective controls using Lipofectamine RNAiMAX (Invitrogen) according to manufacturer's instructions. miR mimics and inhibitors were purchased from Life Technologies or Exiqon.

In Vivo Assays 8-10 week old Balb/C mice (The Jackson Laboratory) were injected subcutaneously with $5 \times 10^5$ tumor cells in Matrigel (BD) per each flank. Tumor growth was measured with calipers, with volume computed as $\frac{1}{2}*Length*Width^2$. Mice were randomized into groups once the average tumor volume reached 100 mm$^3$, approximately 7-10 days after injection. miR inhibitors were delivered i.v. in either PBS or vascular targeted 7C1 nanoparticles every two days from randomization for a total of three doses.

Irradiation

Cells or mice were irradiated on a Shepherd Cesium-137 irradiator at a rate of approximately 1.34 cGy per minute. In tumor-targeted radiation experiments, mice were restrained in a lead shield (Brain Tree Scientific) to minimize exposure to the non-tumor areas.

Cell Titer Glo/Caspase Glo

Cells were transfected in a 6 well plate with miR-15a-5p mimic or inhibitor, and the corresponding controls from Exiqon (Qiagen) as previously described. Cells were transferred to a 96 well plate 16 hours post-transfection (1000 cells/well). In some studies, at 24 h post-transfection the cells were irradiated with 0, 2, or 5 Gy. Cell Titer-Glo and Caspase 3/7 Glo were analyzed at 48 h and 96 h, according to manufacturer's instructions.

Statistics.

All statistical analysis was performed using Excel (Microsoft) or Prism (GraphPad). Two-tailed Student's T-test or ANOVA with post-hoc corrections was used to calculate statistical significance. P values <0.05 were considered significant.

Results

SMPD1 Expression Correlates with Better Overall Survival in Cancer.

We first evaluated the expression of SMPD1 in human cancers and asked if the levels of SMPD1 correlated with overall survival (FIG. 13) using the online database Kaplan-Meier Plotter (kmplotter, at kmplot.com/analysis/). We observed that in breast and ovarian cancers, SMPD1 high patients had significantly better overall survival (FIG. 13A, 13B). In lung cancer patients, data was available for patients that only received radiation therapy. In this subset, SMPD1 high patients had almost two-fold better overall survival than patients with low SMPD1 (FIG. 13C). Analysis of TOGA revealed that SMPD1 is seldom mutated or amplified, suggesting transcriptional and/or post-transcriptional mechanisms control the expression of SMPD1.

miRs Regulating SMPD1 Exhibit Differential Dose Expression

Given that miRs are a major mechanism for post-transcriptional control of gene expression, we sought to identify miRs that specifically targeted SMPD1. TargetScan analysis of the SMPD1 3' untranslated region identified miR-15 family as putative regulators of SMPD1 (FIG. 14A). We chose to evaluate this using ECs as a model system since they express ~20 fold more SMPD1 than tumor cells. We asked if there was any miR-15a family member that was differentially regulated by radiation. HUVECs were treated with either a single 2 Gy or 20 Gy dose via Cs-137 and miRs were profiled at 6 h post treatment. miR-15a exhibited the greatest differential change at 6 hours post-IR between exposure of 2 Gy and 20 Gy radiation relative to non-irradiated samples (FIG. 14B). We first confirmed that endogenous miR-15a decreased at high dose radiation and the expression of SMPD1 was reciprocal to the amount of miR-15a (FIG. 15A) via qRT-PCR. Subsequently, we confirmed that exogenous transfection of miR-15a significantly reduced expression of SMPD1 mRNA (FIG. 15B) and protein levels (FIG. 15C). These observations establish that miR-15a is differentially expressed at low vs high dose radiation and affects SMPD1 levels in ECs.

Since our data indicates that high dose radiation decreased miR-15a and increased SMPD1, we asked if inhibition of miR-15a affected cell viability. HUVECs transfected with miR-15a inhibitor demonstrated dramatically decreased cell proliferation at 48 h and increased Caspase activation 24 h post radiation (FIG. 16A-B). While noting SMPD1 is characterized by a 20 fold increased expression in ECs relative to other cell types (De Meerleer et al., The Lancet Oncology. 2014; 15(4):e170-e7), we analyzed the effects of miR-15a inhibitor on apoptosis in a similar fashion in malignant cell lines focusing on colorectal cell lines. Similar to HUVECs, miR-15a inhibitor dramatically decreased cell viability in HCT-116 cells and CT26 cells (FIG. 17A). We observed that consistent with other reports, miR-15a inhibition affected inflammatory signaling in ECs by increasing IP10 (CXCL10) levels (FIG. 17A), enhancing caspase-1 inflammasome activation (FIG. 17B) and increasing the expression of Gasdermin D (FIG. 17C), a key regulator of pyroptosis (Kovacs et al., Trends in Cell Biology. 27(9):673-84). Pyroptosis is a lytic, regulated cell death that requires the enzymatic activity of inflammatory caspases. Since pyroptosis releases intracellular danger associated molecular patterns (DAMPs) and cytokines such as IL-113, it is thought to be a more immunogenic form of cell death (Kolb et al., Trends in Immunology. 38(10):705-18).

Inhibition of miR-15a in the Vasculature Decreases Tumor Growth and Angiogenesis We next assessed whether miR-15a inhibitor had any effects on tumor growth in vivo and if these effects were dependent on its regulation of angiogenesis. In a murine CT26 colorectal carcinoma flank tumor model, systemic treatment with i.v. injected miR-15a inhibitor resulted in an approximately 50% decrease in tumor growth after 7 days (FIG. 18A). Since our in vitro experiments demonstrated miR-15a inhibition also affected CT26 proliferation, it is possible that this tumor delay was a result of direct tumor cell inhibition. To address this, we took advantage of a vascular-targeted nanoparticle that we have established as an efficient platform for delivering miRs to tumor vasculature and not tumor cells. We found that delivery of vascular-targeted miR-15a inhibitor in the same model was sufficient to decrease tumor burden (FIG. 18B). Importantly, the tumors treated with miR-15a inhibitor had a significant decrease in angiogenesis as measured by CD31 area (FIG. 18C). Taken together, our observations indicate that miR-15a, a regulator of SMPD1, is inhibited by high dose radiation in ECs. A synthetic miR-15a inhibitor not only decreased EC proliferation in vitro but also decreased angiogenesis and tumor growth in vivo.

The importance of the TME in radiation has been elucidated with the advent of new technologies and techniques allowing safer radiation dose escalation that engages the TME components (Barker et al., Nat Rev Cancer. 2015 July; 15(7):409-25). Kolesnick et al) were among the first to demonstrate the importance of dose magnitude in eliciting rapid endothelial apoptosis via SMPD1 translocation to the plasma membrane. This translocation of SMPD1 produced ceramide thereby facilitating enhanced FAS-FASL and TNFRSF10-TNFLSF10 apoptotic signaling (De Meerleer et al., The Lancet Oncology. 2014; 15(4):e170-e7). While earlier pre-clinical models focused attention on single high dose radiation, this is not directly clinically applicable to most disease sites given dose limitations to adjacent critical organs. With this constraint, total radiation dose is divided over several days to allow sublethal damage repair of normal tissue. Using a syngeneic CT26 colorectal cancer model, Zhu et al compared fractionation between 6 Gy×5 fractions and 12 Gy×3 fractions. In the 6 Gy cohort, only a cumulative dose of 12 Gy or higher led to incremental increased SMPD1 activity, increased endothelial cell apoptosis, and decreased microvessel density. In contrast, multiple administrations of 12 Gy did not significantly change SMPD1 function or EC apoptosis rates (Zhu et al., Asian Pac J Cancer Prev. 2015; 16(11):4543-8).

As radiation dose dictates SMPD1 activity, as well as the expression of distinct miRs, we asked whether miRs with predicted binding to the SMPD1 3'-UTR also exhibited dose dependent differential expression. Interestingly, among our miRNA microarray, there were three miRs targeting SMPD1, which increased with higher doses of radiation. However, just a single miR, miR-15a was increased nearly 2-fold at 2 Gy and decreased significantly with the ablative dose radiation of 20 Gy. Recent insight into vascular miR-15a, elucidates oxidative stress as an inhibitor of miR-15a expression and the subsequent rise in SMPD1 activity. In retinal ECs, Wang et al confirmed that miR-15a binds directly to the 3'-UTR of SMPD1, and also that miR-15a inhibition significantly increases ceramide production. Indeed, miR-15a inhibition has been shown to increase expression of pro-inflammatory cytokines such as IL-6, IL-1β, and TNF-α (Wang et al., E Bio Medicine. 2016; 11:138-50) and increased leukostasis, elevated CD45, and NF-κB levels (Ye et al., Journal of Neuroinflammation. 2016 2016; 13(1)) in different pathophysiological contexts.

In the oncogenic context, miR-15a inhibition has been shown to enhance the innate immune response in favor of anti-tumor immunity. Yang et al (International Journal of Cancer. 2017; 141(10):2082-92) found that miR-15a deficiency inhibited tumor growth and prolonged survival in an orthotopic glioma model. In these experiments, they demonstrated miR-15a deficiency led to an influx of CD8+ T cells, decreased expression of inhibitory receptors including PD-1, Tim-3, and LAG-3, and increased inflammatory cytokine production.

Given the heterogeneity of cancer and versatile nature of miRs, miR-15a's role as either an oncogenic miR or a tumor suppressive miR does not lie firmly within one category. Several cancer including non-small cell lung cancer and breast cancer, express lower miR-15a levels. This decrease in the miR has been linked to increased tumor growth and radioresistance that is reversible through miR-15a overexpression (Lan et al., International Journal of Radiation Oncology*Biology*Physics. 2015 2015; 91(1); and Mei et al., Radiation Research. 2015 2015; 183(2)). In colorectal cancer, a recent analysis of 182 patients found that miR-15a overexpression is associated with a worse 5-year progression free survival and overall survival (68% vs 88%, p=0.001; 60% vs 74%, p=0.035, respectively) (Kontos et al., Mol Diagn Ther. 2017 August; 21(4):453-64). However, the dichotomic behavior is not unique to miR-15a, being a largely an oversimplified classification for this molecule able to regulate multiple targets in a context dependent fashion (Svoronos et al. Cancer Research. 2016; 76(13): 3666-70).

What is claimed:

1. A method of enhancing the effect of radiation therapy in a human with a colorectal cancer undergoing radiation therapy, the method comprising administering to a human in need thereof a pharmaceutically effective amount of an antisense oligonucleotide inhibitor of miR-15a.

2. The method of claim 1, wherein the inhibitor of miR-15a is an oligonucleotide of SEQ ID NO. 1.

3. The method of claim 1, wherein the inhibitor of miR-15a is an oligonucleotide having a sequence selected from the group of:
   a) CACAAACCAUUAUGU (positions 1-15 of SEQ ID NO: 1); ACAAACCAUUAUGUG (positions 2-16 of SEQ ID NO: 1); CAAACCAUUAUGUGC (positions 3-17 of SEQ ID NO: 1); AAACCAUUAUGUGCU (positions 4-18 of SEQ ID NO: 1); AACCAUUAUGUGCUG (positions 5-19 of SEQ ID NO: 1); ACCAUUAUGUGCUGC (positions 6-20 of SEQ ID NO: 1); CCAUUAUGUGCUGCU (positions 7-21 of SEQ ID NO: 1); and CAUUAUGUGCUGCUA (positions 8-22 of SEQ ID NO: 1);
   b) CACAAACCAUUAUG (positions 1-14 of SEQ ID NO: 1); ACAAACCAUUAUGU (positions 2-15 of SEQ ID NO: 1); CAAACCAUUAUGUG (positions 3-16 of SEQ ID NO: 1); AAACCAUUAUGUGC (positions 4-17 of SEQ ID NO: 1); AACCAUUAUGUGCU (positions 5-18 of SEQ ID NO: 1); ACCAUUAUGUGCUG (positions 6-19 of SEQ ID NO: 1); CCAUUAUGUGCUGC (positions 7-20 of SEQ ID NO: 1); CAUUAUGUGCUGCU (positions 8-21 of SEQ ID NO: 1); and AUUAUGUGCUGCUA (positions 9-22 of SEQ ID NO: 1);
   c) CACAAACCAUUAU (positions 1-13 of SEQ ID NO: 1); ACAAACCAUUAUG (positions 2-14 of SEQ ID NO: 1); CAAACCAUUAUGU (positions 3-15 of SEQ ID NO: 1); AAACCAUUAUGUG (positions 4-16 of SEQ ID NO: 1); AACCAUUAUGUGC (positions 5-17 of SEQ ID NO: 1); ACCAUUAUGUGCU (positions 6-18 of SEQ ID NO: 1); CCAUUAUGUGCUG (positions 7-19 of SEQ ID NO: 1); CAUUAUGUGCUGC (positions 8-20 of SEQ ID NO: 1); AUUAUGUGCUGCU (positions 9-21 of SEQ ID NO: 1); UUAUGUGCUGCUA (positions 10-22 of SEQ ID NO: 1);
   d) CACAAACCAUUA (positions 1-12 of SEQ ID NO: 1); ACAAACCAUUAU (positions 2-13 of SEQ ID NO: 1); CAAACCAUUAUG (positions 3-14 of SEQ ID NO: 1); AAACCAUUAUGU (positions 4-15 of SEQ ID NO: 1); AACCAUUAUGUG (positions 5-16 of SEQ ID NO: 1); ACCAUUAUGUGC (positions 6-17 of SEQ ID NO: 1); CCAUUAUGUGCU (positions 7-18 of SEQ ID NO: 1); CAUUAUGUGCUG (positions 8-19 of SEQ ID NO: 1); AUUAUGUGCUGC (positions 9-20 of SEQ ID NO: 1); UUAUGUGCUGCU (positions 10-21 of SEQ ID NO: 1); and UAUGUGCUGCUA (positions 11-22 of SEQ ID NO: 1);
   e) CACAAACCAUU (positions 1-11 of SEQ ID NO: 1); ACAAACCAUUA (positions 2-12 of SEQ ID NO: 1); CAAACCAUUAU (positions 3-13 of SEQ ID NO: 1); AAACCAUUAUG (positions 4-14 of SEQ ID NO: 1); AACCAUUAUGU (positions 5-15 of SEQ ID NO: 1); ACCAUUAUGUG (positions 6-16 of SEQ ID NO: 1); CCAUUAUGUGC (positions 7-17 of SEQ ID NO: 1); CAUUAUGUGCU (positions 8-18 of SEQ ID NO: 1); AUUAUGUGCUG (positions 9-20 of SEQ ID NO: 1); UUAUGUGCUGC (positions 10-20 of SEQ ID NO: 1); UAUGUGCUGCU (positions 11-21 of SEQ ID NO: 1); and AUGUGCUGCUA (positions 12-22 of SEQ ID NO: 1);
   f) CACAAACCAU (positions 1-10 of SEQ ID NO: 1); ACAAACCAUU (positions 2-11 of SEQ ID NO: 1); CAAACCAUUA (positions 3-12 of SEQ ID NO: 1); AAACCAUUAU (positions 4-13 of SEQ ID NO: 1); AACCAUUAUG (positions 5-14 of SEQ ID NO: 1); ACCAUUAUGU (positions 6-15 of SEQ ID NO: 1); CCAUUAUGUG (positions 7-16 of SEQ ID NO: 1); CAUUAUGUGC (positions 8-17 of SEQ ID NO: 1); AUUAUGUGCU (positions 9-18 of SEQ ID NO: 1); UUAUGUGCUG (positions 10-19 of SEQ ID NO: 1); UAUGUGCUGC (positions 11-20 of SEQ ID NO: 1); AUGUGCUGCU (positions 12-21 of SEQ ID NO: 1); and UGUGCUGCUA (positions 13-22 of SEQ ID NO: 1);
   g) CACAAACCA (positions 1-9 of SEQ ID NO: 1); ACAAACCAU (positions 2-10 of SEQ ID NO: 1); CAAACCAUU (positions 3-11 of SEQ ID NO: 1); AAACCAUUA (positions 4-12 of SEQ ID NO: 1); AACCAUUAU (positions 5-13 of SEQ ID NO: 1); ACCAUUAUG (positions 6-14 of SEQ ID NO: 1); CCAUUAUGU (positions 7-15 of SEQ ID NO: 1); CAUUAUGUG (positions 8-16 of SEQ ID NO: 1); AUUAUGUGC (positions 9-17 of SEQ ID NO: 1); UUAUGUGCU (positions 10-18 of SEQ ID NO: 1); UAUGUGCUG (positions 11-19 of SEQ ID NO: 1); AUGUGCUGC (positions 12-20 of SEQ ID NO: 1); UGUGCUGCU (positions 13-21 of SEQ ID NO: 1); and GUGCUGCUA (positions 14-22 of SEQ ID NO: 1).

4. The method of claim 1 wherein radiation is administered to the human in need thereof at a dose of from 0.5-5 Gy.

5. The method of claim 4 wherein radiation is administered to the human in need thereof at a dose of from 5-10 Gy.

6. The method of claim 4 wherein radiation is administered to the human in need thereof at a dose of from 10-15 Gy.

7. The method of claim 4 wherein radiation is administered to the human in need thereof at a dose of from 15-20 Gy.

8. A method of enhancing radiation-induced endothelial apoptosis in a human with colorectal cancer undergoing radiation therapy, the method comprising administering to a human in need thereof a pharmaceutically effective amount of an antisense oligonucleotide inhibitor of miR-15a.

9. The method of claim 8, wherein the inhibitor of miR-15a is an oligonucleotide of SEQ ID NO. 1.

10. The method of claim 8, wherein the inhibitor of miR-15a is an oligonucleotide have a sequence selected from the group of:
   a) CACAAACCAUUAUGU (positions 1-15 of SEQ ID NO: 1); ACAAACCAUUAUGUG (positions 2-16 of SEQ ID NO: 1); CAAACCAUUAUGUGC (positions 3-17 of SEQ ID NO: 1); AAACCAUUAUGUGCU (positions 4-18 of SEQ ID NO: 1); AACCAUUAUGUGCUG (positions 5-19 of SEQ ID NO: 1); ACCAUUAUGUGCUGC (positions 6-20 of SEQ ID NO: 1); CCAUUAUGUGCUGCU (positions 7-21 of SEQ ID NO: 1); and CAUUAUGUGCUGCUA (positions 8-22 of SEQ ID NO: 1);
   b) CACAAACCAUUAUG (positions 1-14 of SEQ ID NO: 1); ACAAACCAUUAUGU (positions 2-15 of SEQ ID NO: 1); CAAACCAUUAUGUG (positions 3-16 of SEQ ID NO: 1); AAACCAUUAUGUGC (positions 4-17 of SEQ ID NO: 1); AACCAUUAU-GUGCU (positions 5-18 of SEQ ID NO: 1); ACCAUUAUGUGCUG (positions 6-19 of SEQ ID NO: 1); CCAUUAUGUGCUGC (positions 7-20 of SEQ ID NO: 1); CAUUAUGUGCUGCU (positions 8-21 of SEQ ID NO: 1); and AUUAUGUGCUGCUA (positions 9-22 of SEQ ID NO: 1);

c) CACAAACCAUUAU (positions 1-13 of SEQ ID NO: 1); ACAAACCAUUAUG (positions 2-14 of SEQ ID NO: 1); CAAACCAUUAUGU (positions 3-15 of SEQ ID NO: 1); AAACCAUUAUGUG (positions 4-16 of SEQ ID NO: 1); AACCAUUAUGUGC (positions 5-17 of SEQ ID NO: 1); ACCAUUAUGUGCU (positions 6-18 of SEQ ID NO: 1); CCAUUAUGUGCUG (positions 7-19 of SEQ ID NO: 1); CAUUAUGUGCUGC (positions 8-20 of SEQ ID NO: 1); AUUAU-GUGCUGCU (positions 9-21 of SEQ ID NO: 1); UUAUGUGCUGCUA (positions 10-22 of SEQ ID NO: 1);

d) CACAAACCAUUA (positions 1-12 of SEQ ID NO: 1); ACAAACCAUUAU (positions 2-13 of SEQ ID NO: 1); CAAACCAUUAUG (positions 3-14 of SEQ ID NO: 1); AAACCAUUAUGU (positions 4-15 of SEQ ID NO: 1); AACCAUUAUGUG (positions 5-16 of SEQ ID NO: 1); ACCAUUAUGUGC (positions 6-17 of SEQ ID NO: 1); CCAUUAUGUGCU (positions 7-18 of SEQ ID NO: 1); CAUUAUGUGCUG (positions 8-19 of SEQ ID NO: 1); AUUAU-GUGCUGC (positions 9-20 of SEQ ID NO: 1); UUAUGUGCUGCU (positions 10-21 of SEQ ID NO: 1); and UAUGUGCUGCUA (positions 11-22 of SEQ ID NO: 1);

e) CACAAACCAUU (positions 1-11 of SEQ ID NO: 1); ACAAACCAUUA (positions 2-12 of SEQ ID NO: 1); CAAACCAUUAU (positions 3-13 of SEQ ID NO: 1); AAACCAUUAUG (positions 4-14 of SEQ ID NO: 1); AACCAUUAUGU (positions 5-15 of SEQ ID NO: 1); ACCAUUAUGUG (positions 6-16 of SEQ ID NO: 1); CCAUUAUGUGC (positions 7-17 of SEQ ID NO: 1); CAUUAUGUGCU (positions 8-18 of SEQ ID NO: 1); AUUAUGUGCUG (positions 9-20 of SEQ ID NO: 1); UUAUGUGCUGC (positions 10-20 of SEQ ID NO: 1); UAUGUGCUGCU (positions 11-21 of SEQ ID NO: 1); and AUGUGCUGCUA (positions 12-22 of SEQ ID NO: 1);

f) CACAAACCAU (positions 1-10 of SEQ ID NO: 1); ACAAACCAUU (positions 2-11 of SEQ ID NO: 1); CAAACCAUUA (positions 3-12 of SEQ ID NO: 1); AAACCAUUAU (positions 4-13 of SEQ ID NO: 1); AACCAUUAUG (positions 5-14 of SEQ ID NO: 1); ACCAUUAUGU (positions 6-15 of SEQ ID NO: 1); CCAUUAUGUG (positions 7-16 of SEQ ID NO: 1); CAUUAUGUGC (positions 8-17 of SEQ ID NO: 1); AUUAUGUGCU (positions 9-18 of SEQ ID NO: 1); UUAUGUGCUG (positions 10-19 of SEQ ID NO: 1); UAUGUGCUGC (positions 11-20 of SEQ ID NO: 1); AUGUGCUGCU (positions 12-21 of SEQ ID NO: 1); and UGUGCUGCUA (positions 13-22 of SEQ ID NO: 1);

g) CACAAACCA (positions 1-9 of SEQ ID NO: 1); ACAAACCAU (positions 2-10 of SEQ ID NO: 1); CAAACCAUU (positions 3-11 of SEQ ID NO: 1); AAACCAUUA (positions 4-12 of SEQ ID NO: 1); AACCAUUAU (positions 5-13 of SEQ ID NO: 1); ACCAUUAUG (positions 6-14 of SEQ ID NO: 1); CCAUUAUGU (positions 7-15 of SEQ ID NO: 1); CAUUAUGUG (positions 8-16 of SEQ ID NO: 1); AUUAUGUGC (positions 9-17 of SEQ ID NO: 1); UUAUGUGCU (positions 10-18 of SEQ ID NO: 1); UAUGUGCUG (positions 11-19 of SEQ ID NO: 1); AUGUGCUGC (positions 12-20 of SEQ ID NO: 1); UGUGCUGCU (positions 13-21 of SEQ ID NO: 1); and GUGCUGCUA (positions 14-22 of SEQ ID NO: 1).

11. The method of claim 8 wherein radiation of the radiation therapy is administered to the human at a dose of from 0.5-5 Gy.

12. The method of claim 8, wherein the miR-15a inhibitor is administered using a hepatic arterial infusion pump.

13. The method of claim 8 wherein radiation is administered to the human in need thereof at a dose of from 5-10 Gy.

14. The method of claim 8 wherein radiation is administered to the human in need thereof at a dose of from 10-15 Gy.

15. The method of claim 8 wherein radiation is administered to the human in need thereof at a dose of from 15-20 Gy.

* * * * *